United States Patent
Guerrini et al.

(10) Patent No.: US 8,227,414 B2
(45) Date of Patent: Jul. 24, 2012

(54) HIGHLY POTENT FULL AND PARTIAL AGONISTS AND ANTAGONISTS OF THE NOCICEPTIN/ORPHANIN FQ RECEPTOR

(75) Inventors: Remo Guerrini, Ferrara (IT); Severo Salvadori, Ferrara (IT); Girolamo Calo', Ferrara (IT); Domenico Regoli, Ferrara (IT)

(73) Assignee: UFPEPTIDES S.R.L., Ferrara (FE) (IT)

( * ) Notice: Subject to any disclaimer, the term of this patent is extended or adjusted under 35 U.S.C. 154(b) by 1072 days.

(21) Appl. No.: 11/884,241

(22) PCT Filed: Feb. 15, 2006

(86) PCT No.: PCT/EP2006/050958
§ 371 (c)(1),
(2), (4) Date: Jun. 17, 2008

(87) PCT Pub. No.: WO2006/087340
PCT Pub. Date: Aug. 24, 2006

(65) Prior Publication Data
US 2010/0273710 A1    Oct. 28, 2010

(30) Foreign Application Priority Data
Feb. 15, 2005   (IT) ............................... FE2005A0003

(51) Int. Cl.
*A61K 38/10*    (2006.01)

(52) U.S. Cl. .................. 514/15.7; 514/4.9; 530/326

(58) Field of Classification Search ................. None
See application file for complete search history.

(56) References Cited

FOREIGN PATENT DOCUMENTS

| EP | 1 422 240 A2 | | 5/2004 |
|---|---|---|---|
| IT | A-1 422 240 | * | 5/2004 |
| WO | WO 03/093294 A2 | | 11/2003 |
| WO | WO 2005/004896 | * | 1/2005 |
| WO | WO 2005/004896 A1 | | 1/2005 |

OTHER PUBLICATIONS

Chang et al., Regulatory peptides, 2005, vol. 130, No. 3, pp. 116-122.*
Tancredi et al., Chemistry, Feb. 2005, vol. 11, No. 7, pp. 2061-2070.*
Tancredi et al., "The Interaction of HIghly Helical Structural Mutants with the NOP Receptor Discloses the Role of . . . ," Chem. Eur. J. 2005, 11, 2061-2070.
Zhang et al., "Novel, Potent ORL-1 Receptor Agonist Peptides Containing-Helix-Promoting Conformational Constraints," J. Med. Chem. 2002, 45, 5280-5286.
Calo et al; [Nphe1, Arg14, Lys15]Nociceptin-NH2, a novel potent and selective antagonist of the nociceptin/orphanin FQ receptor; British Journal of Pharmacology (2002) 136, 303-311.

\* cited by examiner

Primary Examiner — Christopher R. Tate
Assistant Examiner — Roy Teller
(74) Attorney, Agent, or Firm — Abelman, Frayne & Schwab

(57) ABSTRACT

Peptide analogs of nociceptin/orphanin FQ, compositions thereof, and their use in treatment of disorders and dysfunctions related to activation or blocking of NOP receptors are described.

11 Claims, 3 Drawing Sheets

SEQUENCE LISTING

<160> NUMBER OF SEQ ID NOS: 102

<210> SEQ ID NO 1
<211> LENGTH: 17
<212> TYPE: PRT
<213> ORGANISM: Artificial Sequence
<220> FEATURE:
<223> OTHER INFORMATION: synthetized
<220> FEATURE:

```
<221> NAME/KEY: MOD_RES
<222> LOCATION: (1)..(1)
<223> OTHER INFORMATION: Xaa= N-benzyl glycine
<220> FEATURE:
<221> NAME/KEY: MOD_RES
<222> LOCATION: (7)..(7)
<223> OTHER INFORMATION: Xaa = Aib

<400> SEQUENCE: 1

Xaa Gly Gly Phe Thr Gly Xaa Arg Lys Ser Ala Arg Lys Arg Lys Asn
 1               5                  10                  15

Gln

<210> SEQ ID NO 2
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib

<400> SEQUENCE: 2

Phe Gly Gly Phe Thr Gly Xaa Arg Lys Ser Ala Arg Lys Arg Lys Asn
 1               5                  10                  15

Gln

<210> SEQ ID NO 3
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib

<400> SEQUENCE: 3

Phe Gly Gly Phe Thr Gly Xaa Arg Lys Ser Ala Arg Lys Arg Lys Asn
 1               5                  10                  15

Gln

<210> SEQ ID NO 4
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is fluorinated
```

```
<220> FEATURE:
<221> NAME/KEY: MOD_RES
<222> LOCATION: (7)..(7)
<223> OTHER INFORMATION: Xaa = Aib

<400> SEQUENCE: 4

Phe Gly Gly Phe Thr Gly Xaa Arg Lys Ser Ala Arg Lys Arg Lys Asn
1               5                   10                  15

Gln

<210> SEQ ID NO 5
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib

<400> SEQUENCE: 5

Xaa Gly Gly Phe Thr Gly Xaa Arg Lys Ser Ala Arg Lys Arg Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib

<400> SEQUENCE: 6

Phe Gly Gly Phe Thr Gly Xaa Arg Lys Ser Ala Arg Lys Arg Lys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib

<400> SEQUENCE: 7

Phe Gly Gly Phe Thr Gly Xaa Arg Lys Ser Ala Arg Lys Arg Lys
1               5                   10                  15
```

```
<210> SEQ ID NO 8
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib

<400> SEQUENCE: 8

Phe Gly Gly Phe Thr Gly Xaa Arg Lys Ser Ala Arg Lys Arg Lys
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 9

Xaa Gly Gly Phe Thr Gly Xaa Arg Lys Ser Xaa Arg Lys Arg Lys Asn
1               5                   10                  15

Gln

<210> SEQ ID NO 10
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 10

Phe Gly Gly Phe Thr Gly Xaa Arg Lys Ser Xaa Arg Lys Arg Lys Asn
1               5                   10                  15

Gln

<210> SEQ ID NO 11
```

```
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Aib

<400> SEQUENCE: 11

Phe Gly Gly Phe Thr Gly Xaa Arg Lys Ser Xaa Arg Lys Arg Lys Asn
1               5                   10                  15

Gln

<210> SEQ ID NO 12
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 12

Phe Gly Gly Phe Thr Gly Xaa Arg Lys Ser Xaa Arg Lys Arg Lys Asn
1               5                   10                  15

Gln

<210> SEQ ID NO 13
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib
```

-continued

```
<400> SEQUENCE: 13

Xaa Gly Gly Phe Thr Gly Xaa Arg Lys Ser Xaa Arg Lys Arg Lys
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 14

Phe Gly Gly Phe Thr Gly Xaa Arg Lys Ser Xaa Arg Lys Arg Lys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 15

Phe Gly Gly Phe Thr Gly Xaa Arg Lys Ser Xaa Arg Lys Arg Lys
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
```

```
<222> LOCATION: (11)..(11)
<223> OTHER INFORMATION: Xaa = Aib

<400> SEQUENCE: 16

Phe Gly Gly Phe Thr Gly Xaa Arg Lys Ser Xaa Arg Lys Arg Lys
1               5                   10                  15

<210> SEQ ID NO 17
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Isovaline

<400> SEQUENCE: 17

Xaa Gly Gly Phe Thr Gly Xaa Arg Lys Ser Ala Arg Lys Arg Lys Asn
1               5                   10                  15

Gln

<210> SEQ ID NO 18
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline

<400> SEQUENCE: 18

Phe Gly Gly Phe Thr Gly Xaa Arg Lys Ser Ala Arg Lys Arg Lys Asn
1               5                   10                  15

Gln

<210> SEQ ID NO 19
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline

<400> SEQUENCE: 19

Phe Gly Gly Phe Thr Gly Xaa Arg Lys Ser Ala Arg Lys Arg Lys Asn
1               5                   10                  15

Gln
```

```
<210> SEQ ID NO 20
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline

<400> SEQUENCE: 20

Phe Gly Gly Phe Thr Gly Xaa Arg Lys Ser Ala Arg Lys Arg Lys Asn
1               5                   10                  15

Gln

<210> SEQ ID NO 21
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Isovaline

<400> SEQUENCE: 21

Xaa Gly Gly Phe Thr Gly Xaa Arg Lys Ser Ala Arg Lys Arg Lys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline

<400> SEQUENCE: 22

Phe Gly Gly Phe Thr Gly Xaa Arg Lys Ser Ala Arg Lys Arg Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
```

```
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline

<400> SEQUENCE: 23

Phe Gly Gly Phe Thr Gly Xaa Arg Lys Ser Ala Arg Lys Arg Lys
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline

<400> SEQUENCE: 24

Phe Gly Gly Phe Thr Gly Xaa Arg Lys Ser Ala Arg Lys Arg Lys
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 25

Xaa Gly Gly Phe Thr Gly Xaa Arg Lys Ser Xaa Arg Lys Arg Lys Asn
1               5                   10                  15

Gln

<210> SEQ ID NO 26
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
```

```
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 26

Phe Gly Gly Phe Thr Gly Xaa Arg Lys Ser Xaa Arg Lys Arg Lys Asn
1               5                   10                  15

Gln

<210> SEQ ID NO 27
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 27

Phe Gly Gly Phe Thr Gly Xaa Arg Lys Ser Xaa Arg Lys Arg Lys Asn
1               5                   10                  15

Gln

<210> SEQ ID NO 28
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 28

Phe Gly Gly Phe Thr Gly Xaa Arg Lys Ser Xaa Arg Lys Arg Lys Asn
1               5                   10                  15

Gln

<210> SEQ ID NO 29
<211> LENGTH: 15
<212> TYPE: PRT
```

```
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 29

Xaa Gly Gly Phe Thr Gly Xaa Arg Lys Ser Xaa Arg Lys Arg Lys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 30

Phe Gly Gly Phe Thr Gly Xaa Arg Lys Ser Xaa Arg Lys Arg Lys
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 31

Phe Gly Gly Phe Thr Gly Xaa Arg Lys Ser Xaa Arg Lys Arg Lys
1               5                   10                  15

<210> SEQ ID NO 32
<211> LENGTH: 15
<212> TYPE: PRT
<213> ORGANISM: Artificial Sequence
```

```
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 32

Phe Gly Gly Phe Thr Gly Xaa Arg Lys Ser Xaa Arg Lys Arg Lys
1               5                   10                  15

<210> SEQ ID NO 33
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 33

Xaa Gly Gly Phe Thr Gly Xaa Arg Lys Ser Xaa Arg Lys Arg Lys Asn
1               5                   10                  15

Gln

<210> SEQ ID NO 34
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 34

Phe Gly Gly Phe Thr Gly Xaa Arg Lys Ser Xaa Arg Lys Arg Lys Asn
1               5                   10                  15

Gln

<210> SEQ ID NO 35
```

```
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 35

Phe Gly Gly Phe Thr Gly Xaa Arg Lys Ser Xaa Arg Lys Arg Lys Asn
1               5                   10                  15

Gln

<210> SEQ ID NO 36
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 36

Phe Gly Gly Phe Thr Gly Xaa Arg Lys Ser Xaa Arg Lys Arg Lys Asn
1               5                   10                  15

Gln

<210> SEQ ID NO 37
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline
```

-continued

```
<400> SEQUENCE: 37

Xaa Gly Gly Phe Thr Gly Xaa Arg Lys Ser Xaa Arg Lys Arg Lys
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 38

Phe Gly Gly Phe Thr Gly Xaa Arg Lys Ser Xaa Arg Lys Arg Lys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 39

Phe Gly Gly Phe Thr Gly Xaa Arg Lys Ser Xaa Arg Lys Arg Lys
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is fluorinated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
```

```
<222> LOCATION: (11)..(11)
<223> OTHER INFORMATION: Xaa = Isovaline

<400> SEQUENCE: 40

Phe Gly Gly Phe Thr Gly Xaa Arg Lys Ser Xaa Arg Lys Arg Lys
1               5                   10                  15

<210> SEQ ID NO 41
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib

<400> SEQUENCE: 41

Xaa Gly Gly Phe Thr Gly Xaa Arg Lys Ser Ala Arg Lys Arg Lys Asn
1               5                   10                  15

Gln

<210> SEQ ID NO 42
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib

<400> SEQUENCE: 42

Phe Gly Gly Phe Thr Gly Xaa Arg Lys Ser Ala Arg Lys Arg Lys Asn
1               5                   10                  15

Gln

<210> SEQ ID NO 43
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib

<400> SEQUENCE: 43

Phe Gly Gly Phe Thr Gly Xaa Arg Lys Ser Ala Arg Lys Arg Lys Asn
1               5                   10                  15

Gln
```

<210> SEQ ID NO 44
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib

<400> SEQUENCE: 44

Phe Gly Gly Phe Thr Gly Xaa Arg Lys Ser Ala Arg Lys Arg Lys Asn
1               5                   10                  15

Gln

<210> SEQ ID NO 45
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib

<400> SEQUENCE: 45

Xaa Gly Gly Phe Thr Gly Xaa Arg Lys Ser Ala Arg Lys Arg Lys
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib

<400> SEQUENCE: 46

Phe Gly Gly Phe Thr Gly Xaa Arg Lys Ser Ala Arg Lys Arg Lys
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)

```
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib

<400> SEQUENCE: 47

Phe Gly Gly Phe Thr Gly Xaa Arg Lys Ser Ala Arg Lys Arg Lys
 1               5                  10                  15

<210> SEQ ID NO 48
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib

<400> SEQUENCE: 48

Phe Gly Gly Phe Thr Gly Xaa Arg Lys Ser Ala Arg Lys Arg Lys
 1               5                  10                  15

<210> SEQ ID NO 49
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 49

Xaa Gly Gly Phe Thr Gly Xaa Arg Lys Ser Xaa Arg Lys Arg Lys Asn
 1               5                  10                  15

Gln

<210> SEQ ID NO 50
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
```

```
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 50

Phe Gly Gly Phe Thr Gly Xaa Arg Lys Ser Xaa Arg Lys Arg Lys Asn
1               5                   10                  15

Gln

<210> SEQ ID NO 51
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 51

Phe Gly Gly Phe Thr Gly Xaa Arg Lys Ser Xaa Arg Lys Arg Lys Asn
1               5                   10                  15

Gln

<210> SEQ ID NO 52
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 52

Phe Gly Gly Phe Thr Gly Xaa Arg Lys Ser Xaa Arg Lys Arg Lys Asn
1               5                   10                  15

Gln

<210> SEQ ID NO 53
<211> LENGTH: 15
<212> TYPE: PRT
```

-continued

```
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 53

Xaa Gly Gly Phe Thr Gly Xaa Arg Lys Ser Xaa Arg Lys Arg Lys
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 54

Phe Gly Gly Phe Thr Gly Xaa Arg Lys Ser Xaa Arg Lys Arg Lys
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 55

Phe Gly Gly Phe Thr Gly Xaa Arg Lys Ser Xaa Arg Lys Arg Lys
1               5                   10                  15

<210> SEQ ID NO 56
<211> LENGTH: 15
<212> TYPE: PRT
<213> ORGANISM: Artificial Sequence
```

```
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 56

Phe Gly Gly Phe Thr Gly Xaa Arg Lys Ser Xaa Arg Lys Arg Lys
1               5                   10                  15

<210> SEQ ID NO 57
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Isovaline

<400> SEQUENCE: 57

Xaa Gly Gly Phe Thr Gly Xaa Arg Lys Ser Ala Arg Lys Arg Lys Asn
1               5                   10                  15

Gln

<210> SEQ ID NO 58
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Isovaline

<400> SEQUENCE: 58

Phe Gly Gly Phe Thr Gly Xaa Arg Lys Ser Ala Arg Lys Arg Lys Asn
1               5                   10                  15

Gln

<210> SEQ ID NO 59
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
```

```
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Isovaline

<400> SEQUENCE: 59

Phe Gly Gly Phe Thr Gly Xaa Arg Lys Ser Ala Arg Lys Arg Lys Asn
1               5                   10                  15

Gln

<210> SEQ ID NO 60
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Isovaline

<400> SEQUENCE: 60

Phe Gly Gly Phe Thr Gly Xaa Arg Lys Ser Ala Arg Lys Arg Lys Asn
1               5                   10                  15

Gln

<210> SEQ ID NO 61
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Isovaline

<400> SEQUENCE: 61

Xaa Gly Gly Phe Thr Gly Xaa Arg Lys Ser Ala Arg Lys Arg Lys
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Isovaline
```

```
<400> SEQUENCE: 62

Phe Gly Gly Phe Thr Gly Xaa Arg Lys Ser Ala Arg Lys Arg Lys
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Isovaline

<400> SEQUENCE: 63

Phe Gly Gly Phe Thr Gly Xaa Arg Lys Ser Ala Arg Lys Arg Lys
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Isovaline

<400> SEQUENCE: 64

Phe Gly Gly Phe Thr Gly Xaa Arg Lys Ser Ala Arg Lys Arg Lys
1               5                   10                  15

<210> SEQ ID NO 65
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 65

Xaa Gly Gly Phe Thr Gly Xaa Arg Lys Ser Xaa Arg Lys Arg Lys Asn
1               5                   10                  15
```

Gln

<210> SEQ ID NO 66
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 66

Phe Gly Gly Phe Thr Gly Xaa Arg Lys Ser Xaa Arg Lys Arg Lys Asn
1               5                   10                  15

Gln

<210> SEQ ID NO 67
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Isovaline
<220> FEATURE:
<221> NAME/KEY: MOD_RES
<222> LOCATION: (11)..(11)
<223> OTHER INFORMATION: Aib

<400> SEQUENCE: 67

Phe Gly Gly Phe Thr Gly Xaa Arg Lys Ser Xaa Arg Lys Arg Lys Asn
1               5                   10                  15

Gln

<210> SEQ ID NO 68
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Aib

<400> SEQUENCE: 68

Phe Gly Gly Phe Thr Gly Xaa Arg Lys Ser Xaa Arg Lys Arg Lys Asn
1               5                   10                  15

Gln

<210> SEQ ID NO 69
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 69

Xaa Gly Gly Phe Thr Gly Xaa Arg Lys Ser Xaa Arg Lys Arg Lys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 70

Phe Gly Gly Phe Thr Gly Xaa Arg Lys Ser Xaa Arg Lys Arg Lys
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)

```
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 71

Phe Gly Gly Phe Thr Gly Xaa Arg Lys Ser Xaa Arg Lys Arg Lys
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Isovaline
<220> FEATURE:
<221> NAME/KEY: MOD_RES
<222> LOCATION: (11)..(11)
<223> OTHER INFORMATION: Xaa = Aib

<400> SEQUENCE: 72

Phe Gly Gly Phe Thr Gly Xaa Arg Lys Ser Xaa Arg Lys Arg Lys
1               5                   10                  15

<210> SEQ ID NO 73
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 73

Xaa Gly Gly Phe Thr Gly Xaa Arg Lys Ser Xaa Arg Lys Arg Lys Asn
1               5                   10                  15

Gln

<210> SEQ ID NO 74
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
```

```
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 74

Phe Gly Gly Phe Thr Gly Xaa Arg Lys Ser Xaa Arg Lys Arg Lys Asn
1               5                   10                  15

Gln

<210> SEQ ID NO 75
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 75

Phe Gly Gly Phe Thr Gly Xaa Arg Lys Ser Xaa Arg Lys Arg Lys Asn
1               5                   10                  15

Gln

<210> SEQ ID NO 76
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 76

Phe Gly Gly Phe Thr Gly Xaa Arg Lys Ser Xaa Arg Lys Arg Lys Asn
1               5                   10                  15

Gln

<210> SEQ ID NO 77
<211> LENGTH: 15
<212> TYPE: PRT
```

```
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 77

Xaa Gly Gly Phe Thr Gly Xaa Arg Lys Ser Xaa Arg Lys Arg Lys
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 78

Phe Gly Gly Phe Thr Gly Xaa Arg Lys Ser Xaa Arg Lys Arg Lys
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: misc_feature
<222> LOCATION: (1)..(2)
<223> OTHER INFORMATION: Reduced peptide bond, -CH2-NH-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 79

Phe Gly Gly Phe Thr Gly Xaa Arg Lys Ser Xaa Arg Lys Arg Lys
1               5                   10                  15

<210> SEQ ID NO 80
<211> LENGTH: 15
<212> TYPE: PRT
<213> ORGANISM: Artificial Sequence
```

```
<220> FEATURE:
<223> OTHER INFORMATION: synthetized
<220> FEATURE:
<221> NAME/KEY: misc_feature
<222> LOCATION: (1)..(2)
<223> OTHER INFORMATION: Ester peptide bond, -CH2-O-
<220> FEATURE:
<221> NAME/KEY: MOD_RES
<222> LOCATION: (4)..(4)
<223> OTHER INFORMATION: Para position of phenyl ring is nitrated
<220> FEATURE:
<221> NAME/KEY: MOD_RES
<222> LOCATION: (7)..(7)
<223> OTHER INFORMATION: Xaa = Aib
<220> FEATURE:
<221> NAME/KEY: MOD_RES
<222> LOCATION: (11)..(11)
<223> OTHER INFORMATION: Xaa = Isovaline

<400> SEQUENCE: 80

Phe Gly Gly Phe Thr Gly Xaa Arg Lys Ser Xaa Arg Lys Arg Lys
1               5                   10                  15

<210> SEQ ID NO 81
<211> LENGTH: 17
<212> TYPE: PRT
<213> ORGANISM: Artificial Sequence
<220> FEATURE:
<223> OTHER INFORMATION: synthetized

<400> SEQUENCE: 81

Phe Gly Gly Phe Thr Gly Ala Arg Lys Ser Ala Arg Lys Leu Ala Asn
1               5                   10                  15

Gln

<210> SEQ ID NO 82
<211> LENGTH: 17
<212> TYPE: PRT
<213> ORGANISM: Artificial Sequence
<220> FEATURE:
<223> OTHER INFORMATION: Synthetized. Featured in patent as UFP-101,
      ref. Calò et al. Br J Pharmacol 136, 303-311, 2002
<220> FEATURE:
<221> NAME/KEY: MOD_RES
<222> LOCATION: (1)..(1)
<223> OTHER INFORMATION: Xaa = N-Benzyl glycine

<400> SEQUENCE: 82

Xaa Gly Gly Phe Thr Gly Ala Arg Lys Ser Ala Arg Lys Arg Lys Asn
1               5                   10                  15

Gln

<210> SEQ ID NO 83
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (7)..(7)
<223> OTHER INFORMATION: Xaa = 1-amino-cyclopropan-carboxylic acid

<400> SEQUENCE: 83

Phe Gly Gly Phe Thr Gly Xaa Arg Lys Ser Ala Arg Lys Leu Ala Asn
1               5                   10                  15

Gln

<210> SEQ ID NO 84
```

```
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (7)..(7)
<223> OTHER INFORMATION: Xaa = 1-Amino-cyclopentan-carboxylic acid

<400> SEQUENCE: 84

Phe Gly Gly Phe Thr Gly Xaa Arg Lys Ser Ala Arg Lys Leu Ala Asn
1               5                   10                  15

Gln

<210> SEQ ID NO 85
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (7)..(7)
<223> OTHER INFORMATION: Xaa = 1-Amino-cyclohexane-carboxylic acid

<400> SEQUENCE: 85

Phe Gly Gly Phe Thr Gly Xaa Arg Lys Ser Ala Arg Lys Leu Ala Asn
1               5                   10                  15

Gln

<210> SEQ ID NO 86
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (7)..(7)
<223> OTHER INFORMATION: Methylation of alpha-carbon (D/L)

<400> SEQUENCE: 86

Phe Gly Gly Phe Thr Gly Val Arg Lys Ser Ala Arg Lys Leu Ala Asn
1               5                   10                  15

Gln

<210> SEQ ID NO 87
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (7)..(7)
<223> OTHER INFORMATION: Methylation of alpha-carbon (D/L)

<400> SEQUENCE: 87

Phe Gly Gly Phe Thr Gly Leu Arg Lys Ser Ala Arg Lys Leu Ala Asn
1               5                   10                  15

Gln

<210> SEQ ID NO 88
<211> LENGTH: 17
<212> TYPE: PRT
<213> ORGANISM: Artificial Sequence
<220> FEATURE:
```

```
<223> OTHER INFORMATION: synthetized
<220> FEATURE:
<221> NAME/KEY: MOD_RES
<222> LOCATION: (7)..(7)
<223> OTHER INFORMATION: Isovaline (D/L)
<220> FEATURE:
<221> NAME/KEY: MOD_RES
<222> LOCATION: (7)..(7)
<223> OTHER INFORMATION: Xaa = Isovaline (D/L)

<400> SEQUENCE: 88

Phe Gly Gly Phe Thr Gly Xaa Arg Lys Ser Ala Arg Lys Leu Ala Asn
1               5                   10                  15
Gln

<210> SEQ ID NO 89
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (7)..(7)
<223> OTHER INFORMATION: Xaa = 2-amino-2-ethyl-butyric acid

<400> SEQUENCE: 89

Phe Gly Gly Phe Thr Gly Xaa Arg Lys Ser Ala Arg Lys Leu Ala Asn
1               5                   10                  15
Gln

<210> SEQ ID NO 90
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (7)..(7)
<223> OTHER INFORMATION: Xaa = 2-amino-2-propyl-pentanoic acid

<400> SEQUENCE: 90

Phe Gly Gly Phe Thr Gly Xaa Arg Lys Ser Ala Arg Lys Leu Ala Asn
1               5                   10                  15
Gln

<210> SEQ ID NO 91
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (11)..(11)
<223> OTHER INFORMATION: Xaa = 1-Amino-cyclopropan-carboxylic acid

<400> SEQUENCE: 91

Phe Gly Gly Phe Thr Gly Ala Arg Lys Ser Xaa Arg Lys Leu Ala Asn
1               5                   10                  15
Gln

<210> SEQ ID NO 92
<211> LENGTH: 17
<212> TYPE: PRT
<213> ORGANISM: Artificial Sequence
<220> FEATURE:
```

<223> OTHER INFORMATION: synthetized
<220> FEATURE:
<221> NAME/KEY: MOD_RES
<222> LOCATION: (11)..(11)
<223> OTHER INFORMATION: Xaa = 1-Amino-cyclopentan-carboxylic acid

<400> SEQUENCE: 92

Phe Gly Gly Phe Thr Gly Ala Arg Lys Ser Xaa Arg Lys Leu Ala Asn
1               5                   10                  15

Gln

<210> SEQ ID NO 93
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (11)..(11)
<223> OTHER INFORMATION: Xaa = 1-Amino cyclohexane carboxylic acid

<400> SEQUENCE: 93

Phe Gly Gly Phe Thr Gly Ala Arg Lys Ser Xaa Arg Lys Leu Ala Asn
1               5                   10                  15

Gln

<210> SEQ ID NO 94
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (11)..(11)
<223> OTHER INFORMATION: Methylation at alpha-carbon [D/L]

<400> SEQUENCE: 94

Phe Gly Gly Phe Thr Gly Ala Arg Lys Ser Val Arg Lys Leu Ala Asn
1               5                   10                  15

Gln

<210> SEQ ID NO 95
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (11)..(11)
<223> OTHER INFORMATION: Methylation at alpha-carbon [D/L]

<400> SEQUENCE: 95

Phe Gly Gly Phe Thr Gly Ala Arg Lys Ser Leu Arg Lys Leu Ala Asn
1               5                   10                  15

Gln

<210> SEQ ID NO 96
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (11)..(11)

<223> OTHER INFORMATION: Xaa = Isovaline [D/L]

<400> SEQUENCE: 96

Phe Gly Gly Phe Thr Gly Ala Arg Lys Ser Xaa Arg Lys Leu Ala Asn
1               5                   10                  15

Gln

<210> SEQ ID NO 97
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (11)..(11)
<223> OTHER INFORMATION: Xaa = 2-amino-2-ethyl butyric acid

<400> SEQUENCE: 97

Phe Gly Gly Phe Thr Gly Ala Arg Lys Ser Xaa Arg Lys Leu Ala Asn
1               5                   10                  15

Gln

<210> SEQ ID NO 98
<211> LENGTH: 17
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (11)..(11)
<223> OTHER INFORMATION: Xaa = 2-amino-2-propyl-pentanoic acid

<400> SEQUENCE: 98

Phe Gly Gly Phe Thr Gly Ala Arg Lys Ser Xaa Arg Lys Leu Ala Asn
1               5                   10                  15

Gln

<210> SEQ ID NO 99
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = Phe OR N-Benzylglycine
<220> FEATURE:
<221> NAME/KEY: MISC_FEATURE
<222> LOCATION: (1)..(2)
<223> OTHER INFORMATION: Normal peptide bond, -CO-NH- OR reduced
      peptide bond, -CH2-NH- OR ester peptide bond, -CH2-O-
<220> FEATURE:
<221> NAME/KEY: MOD_RES
<222> LOCATION: (4)..(4)
<223> OTHER INFORMATION: Para position of phenyl ring is hydrogenated
      OR chlorinated OR fluorinated OR brominated OR iodinated OR
      nitrated OR cyanated
<220> FEATURE:
<221> NAME/KEY: MOD_RES
<222> LOCATION: (7)..(7)
<223> OTHER INFORMATION: Xaa = Ala OR Aib OR Iva OR Deg OR Dpg OR
      (C[alpha]-CH3) Leu OR (C[alpha]-CH3) Val OR Ac3c OR Ac5c OR Ac6c
<220> FEATURE:
<221> NAME/KEY: MOD_RES
<222> LOCATION: (11)..(11)
<223> OTHER INFORMATION: Xaa = Ala OR Aib OR Iva OR Deg OR Dpg OR
      (C[alpha]-CH3 Leu) OR (C[alpha]-CH3) Val OR Ac3c OR Ac5c OR Ac6c
<220> FEATURE:

```
<221> NAME/KEY: MOD_RES
<222> LOCATION: (14)..(14)
<223> OTHER INFORMATION: Xaa = Arg OR Lys OR Orn OR omo-arginine OR
      diaminobutyric acid OR diaminoproprionic acid OR Trp
<220> FEATURE:
<221> NAME/KEY: MISC_FEATURE
<222> LOCATION: (15)..(15)
<223> OTHER INFORMATION: Xaa = Arg OR Lys OR Orn OR omo-arginine OR
      diaminobutyric acid OR diaminoproprionic acid OR Trp; all of
      them followed by Asn-Gln OR Asn-Gln with terminal OH group OR
      Asn OR Asn with terminal OH group OR terminal OH OR terminal
      amide group

<400> SEQUENCE: 99

Xaa Gly Gly Phe Thr Gly Xaa Arg Lys Ser Xaa Arg Lys Xaa Xaa
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = Phe OR N-Benzylglycine
<220> FEATURE:
<221> NAME/KEY: MISC_FEATURE
<222> LOCATION: (1)..(2)
<223> OTHER INFORMATION: Normal peptide bond, -CO-NH- OR reduced
      peptide bond, -CH2-NH- OR ester peptide bond, -CH2-O-
<220> FEATURE:
<221> NAME/KEY: MOD_RES
<222> LOCATION: (4)..(4)
<223> OTHER INFORMATION: Para position of phenyl ring is hydrogenated
      OR chlorinated OR fluorinated OR brominated OR iodinated OR
      nitrated OR cyanated
<220> FEATURE:
<221> NAME/KEY: MOD_RES
<222> LOCATION: (7)..(7)
<223> OTHER INFORMATION: Xaa = Aib OR Iva OR Deg OR Dpg OR (C[alpha]-
      CH3) Leu OR (C[alpha]-CH3) Val OR Ac3c OR Ac5c OR Ac6c
<220> FEATURE:
<221> NAME/KEY: MOD_RES
<222> LOCATION: (11)..(11)
<223> OTHER INFORMATION: Xaa = Ala OR Aib OR Iva OR Deg OR Dpg OR
      (C[alpha]-CH3) Leu OR (C[alpha]-CH3) Val OR Ac3c OR Ac5c OR Ac6c
<220> FEATURE:
<221> NAME/KEY: MOD_RES
<222> LOCATION: (14)..(14)
<223> OTHER INFORMATION: Xaa = Arg OR Lys OR Orn OR omo-arginine OR
      diaminobutyric acid OR diaminoproprionic acid OR Trp
<220> FEATURE:
<221> NAME/KEY: MISC_FEATURE
<222> LOCATION: (15)..(15)
<223> OTHER INFORMATION: Xaa = Arg OR Lys OR Orn OR omo-arginine OR
      diaminobutyric acid OR diaminoproprionic acid OR Trp; all of
      them followed by Asn-Gln OR Asn-Gln with terminal OH group OR
      Asn OR Asn with terminal OH group OR terminal OH OR terminal
      amide group

<400> SEQUENCE: 100

Xaa Gly Gly Phe Thr Gly Xaa Arg Lys Ser Xaa Arg Lys Xaa Xaa
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MISC_FEATURE
<222> LOCATION: (1)..(2)
<223> OTHER INFORMATION: Normal peptide bond, -CO-NH- OR reduced
```

```
              peptide bond, -CH2-NH- OR ester peptide bond, -CH2-O-
<220> FEATURE:
<221> NAME/KEY: MOD_RES
<222> LOCATION: (4)..(4)
<223> OTHER INFORMATION: Para position of phenyl ring is hydrogenated
      OR chlorinated OR fluorinated OR brominated OR iodinated OR
      nitrated ORcyanated
<220> FEATURE:
<221> NAME/KEY: MOD_RES
<222> LOCATION: (7)..(7)
<223> OTHER INFORMATION: Xaa = Aib OR Ac5c OR Iva
<220> FEATURE:
<221> NAME/KEY: MOD_RES
<222> LOCATION: (11)..(11)
<223> OTHER INFORMATION: Xaa = Ala OR Aib OR Ac5c OR Iva
<220> FEATURE:
<221> NAME/KEY: MISC_FEATURE
<222> LOCATION: (15)..(15)
<223> OTHER INFORMATION: Lys in 15 th position as a C-term amino acid
      OR followed by Asn-Gln OR followed by Asn

<400> SEQUENCE: 101

Phe Gly Gly Phe Thr Gly Xaa Arg Lys Ser Xaa Arg Lys Arg Lys
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: synthetized
<220> FEATURE:
<221> NAME/KEY: MOD_RES
<222> LOCATION: (1)..(1)
<223> OTHER INFORMATION: Xaa = N-Benzyl glycine
<220> FEATURE:
<221> NAME/KEY: MOD_RES
<222> LOCATION: (7)..(7)
<223> OTHER INFORMATION: Xaa = Aib OR Isovaline
<220> FEATURE:
<221> NAME/KEY: MOD_RES
<222> LOCATION: (11)..(11)
<223> OTHER INFORMATION: Xaa = Ala OR Aib OR Isovaline
<220> FEATURE:
<221> NAME/KEY: MISC_FEATURE
<222> LOCATION: (15)..(15)
<223> OTHER INFORMATION: Lys in position 15 as a C-terminal amino acid
      OR followed by Asn-Gln

<400> SEQUENCE: 102

Xaa Gly Gly Phe Thr Gly Xaa Arg Lys Ser Xaa Arg Lys Arg Lys
1               5                   10                  15
```

HIGHLY POTENT FULL AND PARTIAL AGONISTS AND ANTAGONISTS OF THE NOCICEPTIN/ORPHANIN FQ RECEPTOR

FIELD OF THE INVENTION

The present invention relates to nociceptin/orphanin FQ (N/OFQ) peptide analogs capable of modulating the activity of the N/OFQ peptide receptor (NOP receptor), pharmaceutical compositions comprising said peptide analogs and their use for treatment of dysfunctions, pathological conditions or pathological states involving said receptor.

BACKGROUND OF THE INVENTION

In 1994, a new receptor termed ORL1, that is structurally similar to opioid receptors, was cloned; according to recent IUPHAR recommendations, the most appropriate name for this receptor is NOP. Its endogenous ligand (N/OFQ), identified at the end of 1995, is a heptadecapeptide similar to some opioid peptides (e.g. dynorphin A), which however does not bind the classical opioid receptors of mu (MOP), delta (DOP) or kappa (KOP) types. The cellular effects mediated by the NOP receptor are similar to those evoked by classical opioid receptors. From a structural point of view, and from the point of view of signal transduction, the N/OFQ-NOP peptide/receptor system belongs to the opioid family, although it represents a pharmacologically distinct branch. Several studies, carried out between 1996 and 1998, showed that N/OFQ can modulate several functions both in the central nervous system (pain, anxiety, learning, memory, drug abuse, appetite) and at the peripheral level (blood pressure, heart rhythm, kidney, gastrointestinal, genitourinary and respiratory functions) (for further details see Massi et al., *Peptides* 21, 2000).

Starting from 1996, the present inventors carried out studies on the N/OFQ-NOP system, leading to the identification of particular NOP receptor ligands, such as i) N/OFQ(1-13)-$NH_2$, which represents the minimal functional fragment with the same activity of the N/OFQ natural ligand (Calo et al., Eur J Pharmacol 311, R3-5, 1996), ii) N/OFQ-$NH_2$ which produces, especially in vivo, more intense and prolonged effects compared to N/OFQ (Rizzi et al., Naunyn Schmiedebergs Arch Pharmacol 363, 161-165. 2001), iii) [Tyr$^1$]N/OFQ(1-13)-$NH_2$, a mixed agonist which acts on NOP and on the classical opioid receptors (Calo et al., Can J Physiol Pharmacol 75, 713-8, 1997; Varani et al., *Naunyn Schmiedebergs Arch Pharmacol* 360, 270-7, 1999), iv) [Phe$^1$?($CH_2$—NH)Gly$^2$]N/OFQ(1-13)-$NH_2$, a selective NOP receptor ligand which behaves as pure antagonist, partial agonist or even as full agonist, depending on the preparation/assay under study (Guerrini et al., *Br J Pharmacol* 123, 163-5, 1998; Okawa et al., Br J Pharmacol 127, 123-30, 1999)—based on the detailed analysis of pharmacological action of [Phe$^1$?($CH_2$—NH)Gly$^2$]N/OFQ(1-13)-$NH_2$ reported by Calo' et al. (*Peptides* 21, 935-47, 2000), it turns out that this compound is truly a partial NOP agonist, v) [Nphe$^1$]N/OFQ(1-13)-$NH_2$, the first pure competitive antagonist of NOP receptor (Calo et al., *Br J Pharmacol* 129, 1183-93, 2000; Guerrini et al., *J Med Chem* 15, 2805-13, 2000). The action of these ligands have been characterised in several in vitro and in vivo assays (see Calo et al., *Br J Pharmacol* 129, 1261-83, 2000). More recently, the Phe$^4$ residue was replaced with (pF)Phe or (p$NO_2$)Phe, thereby obtaining potent selective NOP agonists (Guerrini et al., *J Med Chem* 44, 3956-64, 2001). Another interesting compound, [Arg$^{14}$,Lys$^{15}$]N/OFQ, was identified as a highly potent agonist (17-fold more potent than N/OFQ), selective for human recombinant NOP receptors expressed in HEK293 cells (Okada et al., *Biochem Biophys Res Commun* 278, 493-8, 2000). The actions of this ligand were further characterized in vitro, using isolated tissues sensitive to N/OFQ, and in vivo in the mouse (Rizzi et al., *J Pharmacol Exp Ther* 300, 57-63, 2002). Moreover, Zhang et al., (Zhang et al., *J Med Chem*, 45, 5280-5286, 2002) described N/OFQ analogs, characterized by a 2-amino-2-methyl-propionic acid (Aib) residue in position 7 and/or 11, replacing Ala residues and producing an increase of ligand affinity and potency. N/OFQ analogs were described in WO 99/07212, WO 97/07208, WO 99/03491, WO 99/03880, and EP 1422240. The utility of this ligand has been reported in the treatment/prevention of diseases related to hyperalgesia, neuroendocrine functions, stress, locomotor activity and anxiety.

Hereafter, the reference sequence of the N/OFQ peptide is the following: H-Phe-Gly-Gly-Phe-Thr-Gly-Ala-Arg-Lys-Ser-Ala-Arg-Lys-Leu-Ala-Asn-Gln-OH

DETAILED DESCRIPTION OF THE INVENTION

Figure 1:
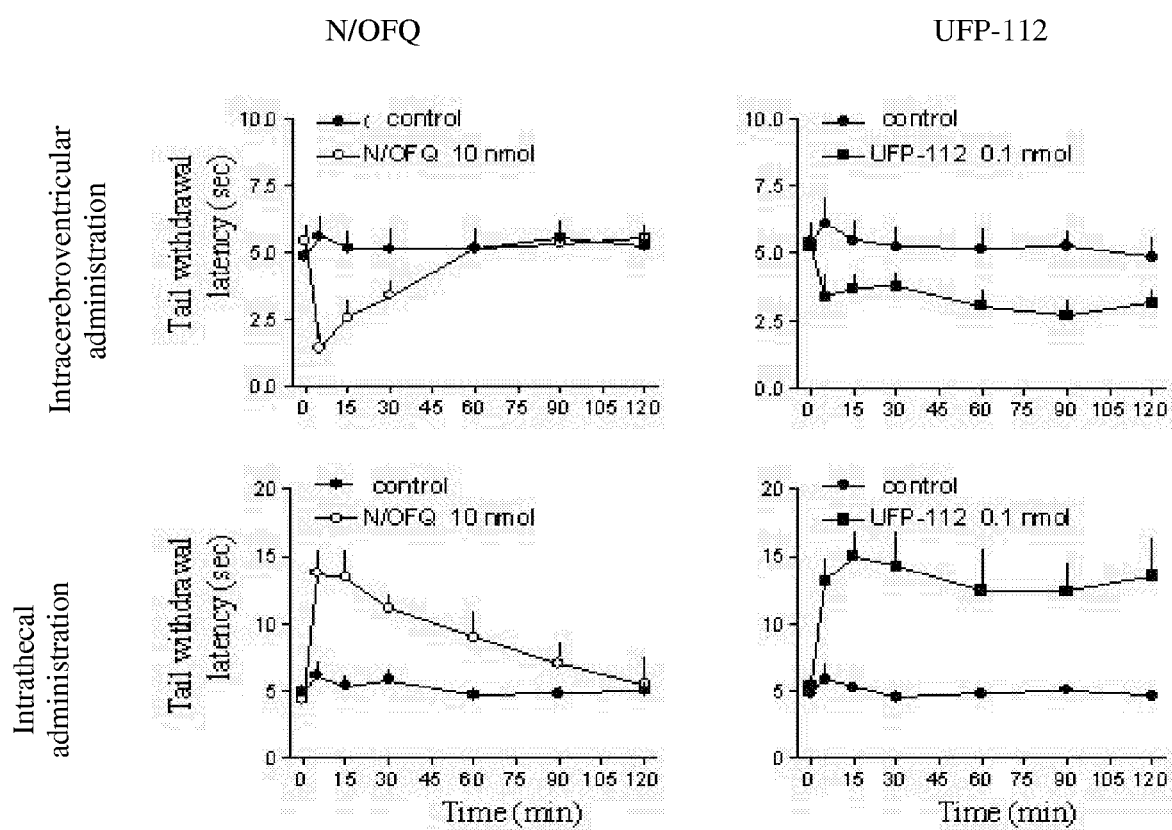
FIG. 1: Effect of intracerebroventricular (i.c.v., as seen in the upper panels) or intrathecal (i.t., as seen in the lower panels) administration of N/OFQ (10 nmol/mouse) and of UFP-112 (0.1 nmol/mouse) in the tail withdrawal assay (ref. Calò et al. Br J Pharmacol. 125, 375-378, 1998). Control animals received one i.c.v. injection of saline (2 µl/mouse). Each point represents the mean±s.e.m. of at least 4 experiments.

The terms used in this patent have a meaning known in the art, as for example in the IUPHAR on Receptor Nomenclature and Drug Classification, Pharm. Rev. (2003) Vol 55, No 4, p. 597, as reported here:

Efficacy—a concept that expresses the degree to which different agonists produce varying responses, even when occupying the same proportion of receptors.

Potency—an expression of the activity of a compound, defined in terms of the concentration or amount needed to produce a defined effect. The potency is measured as $pEC_{50}$ for agonists and as $pA_2$ for antagonists.

Objects of the present invention are N/OFQ peptide analogs, of general formula (I)

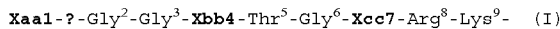
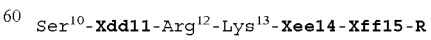

where
Xaa$^1$ is Phe or N-benzyl-glycine (Nphe); ? represents the bond between the first two amino acid residues and is chosen between CO—NH and $CH_2$—NH and $CH_2$—O;
Xbb$^4$ is Phe or (pX)Phe where "X" represents H, Cl, Br, I, F, $NO_2$, CN and "p" indicates the para-position in the phenyl ring of Phe; $Xcc^7$ and $Xdd^{11}$ are chosen between: Ala; 2-amino-2-methyl-propionic acid (Aib); 2-amino-2-methyl-butyric acid (Iva); 2-amino-2-ethyl-butyric (Deg) acid; 2-amino-2-propyl-carboxylic acid (Dpg); $(C_aCH_3)$Leu; $(C_aCH_3)$Val; 1-amino-cyclopropan-carboxylic acid ($Ac_3c$); 1-amino-cyclopentan-carboxylic acid ($Ac_5c$) and 1-amino-cyclohexane-carboxylic acid ($Ac_6c$); $Xee^{14}$ e $Xff^{15}$ are chosen between Arg, Lys, Orn, omoArg, diaminobutyric acid, diaminopropionic acid, or Trp; R represents the dipeptide Asn-Gln-NH$_2$ or Asn-Gln-OH or the amino acid Asn with either an amide (—NH$_2$) or a carboxylic (—OH) terminal group or an amino (—NH$_2$) or a hydroxyl (—OH) terminal group.

Furthermore, the invention includes pharmaceutically acceptable salts of these compounds (I), particularly organic and mineral acid salts such as, hydrochloride, hydrobromide, phosphates, sulphates, acetates, succinates, ascorbates, tartrates, gluconates, benzoates, maleates, fumarates and stearates.

The compounds according to the invention, which fall under formula I, have a proven pharmacological activity, even 100-fold higher than the peptide ligands known in the art. It is therefore possible to hypothesize a synergistic effect of the permutations according to formula I: for positions 1, 4, 7, 11, 14, and 15 and the bond between the first two amino acid residues. A higher activity of the compounds of formula I and particularly of the preferred compounds, preferably agonists and more preferably [(pF)Phe$^4$,Aib$^7$,Arg$^{14}$,Lys$^{15}$]N/OFQ-NH$_2$ is demonstrated with respect to affinity, potency, protease resistance, in vitro kinetics of action, and, above all, duration of their action in vivo.

Preferred compounds are formula (I) compounds, in which ? is CO—NH or CH$_2$—NH or CH$_2$—O, Xaa$^1$ is Phe or Nphe, Xbb$^4$ is Phe or (pX)Phe where "(pX)" is defined as above, Xcc$^7$ and Xdd$^{11}$ are defined as above, Xee$^{14}$ and Xff$^{15}$ are Arg, Lys, Orn, omoArg, or Trp; R is —NH$_2$ or —OH or Asn-NH$_2$ or Asn-OH or Asn-Gln-NH$_2$ or Asn-Gln-OH.

More preferred are those compounds of formula (I) in which ? is CO—NH or CH$_2$—NH or CH$_2$—O; Xaa$^1$ is Phe or Nphe; Xbb$^4$ is Phe or (pF)Phe or (pNO$_2$)Phe; Xcc$^7$ and Xdd$^{11}$ are Ala; 2-amino-2-methyl-propionic acid (Aib); 2-amino-2-methyl-butyric acid (Iva); 2-amino-2-ethyl-butyric (Deg) acid; 2-amino-2-propyl-pentanoic acid (Dpg); (CaCH$_3$)Leu; $(C_aCH3)$Val; 1-amino-cyclopropan-carboxylic acid ($Ac_3c$); 1-amino-cyclopentan-carboxylic acid ($Ac_5c$) and 1-amino-cycloexane-carboxylic acid ($Ac_6c$); Xee$^{14}$ and Xff$^{15}$ are Arg or Lys; R is Asn-Gln-NH$_2$ or —NH$_2$.

Even more preferred are the peptide analogs having formula (I) in which variable residues have the meaning reported in the following table:

|    | Xaa$^1$ | ? | Xbb$^4$ | Xcc$^7$ | Xdd$^{11}$ | Xee$^{14}$ | Xff$^{15}$ | R |
|----|------|-----------|-----------|------|------|-----|-----|---------------|
| 1  | Nphe | CO—NH     | Phe       | Aib  | Ala  | Arg | Lys | Asn-Gln-NH$_2$ |
| 2  | Phe  | CO—NH     | (pF)Phe   | Aib  | Ala  | Arg | Lys | Asn-Gln-NH$_2$ |
| 3  | Phe  | CH$_2$—NH | (pF)Phe   | Aib  | Ala  | Arg | Lys | Asn-Gln-NH$_2$ |
| 4  | Phe  | CH$_2$—O  | (pF)Phe   | Aib  | Ala  | Arg | Lys | Asn-Gln-NH$_2$ |
| 5  | Nphe | CO—NH     | Phe       | Aib  | Ala  | Arg | Lys | —NH$_2$ |
| 6  | Phe  | CO—NH     | (pF)Phe   | Aib  | Ala  | Arg | Lys | —NH$_2$ |
| 7  | Phe  | CH$_2$—NH | (pF)Phe   | Aib  | Ala  | Arg | Lys | —NH$_2$ |
| 8  | Phe  | CH$_2$—O  | (pF)Phe   | Aib  | Ala  | Arg | Lys | —NH$_2$ |
| 9  | Nphe | CO—NH     | Phe       | Aib  | Aib  | Arg | Lys | Asn-Gln-NH$_2$ |
| 10 | Phe  | CO—NH     | (pF)Phe   | Aib  | Aib  | Arg | Lys | Asn-Gln-NH$_2$ |
| 11 | Phe  | CH$_2$—NH | (pF)Phe   | Aib  | Aib  | Arg | Lys | Asn-Gln-NH$_2$ |
| 12 | Phe  | CH$_2$—O  | (pF)Phe   | Aib  | Aib  | Arg | Lys | Asn-Gln-NH$_2$ |
| 13 | Nphe | CO—NH     | Phe       | Aib  | Aib  | Arg | Lys | —NH$_2$ |
| 14 | Phe  | CO—NH     | (pF)Phe   | Aib  | Aib  | Arg | Lys | —NH$_2$ |
| 15 | Phe  | CH$_2$—NH | (pF)Phe   | Aib  | Aib  | Arg | Lys | —NH$_2$ |
| 16 | Phe  | CH$_2$—O  | (pF)Phe   | Aib  | Aib  | Arg | Lys | —NH$_2$ |
| 17 | Nphe | CO—NH     | Phe       | Iva  | Ala  | Arg | Lys | Asn-Gln-NH$_2$ |
| 18 | Phe  | CO—NH     | (pF)Phe   | Iva  | Ala  | Arg | Lys | Asn-Gln-NH$_2$ |
| 19 | Phe  | CH$_2$—NH | (pF)Phe   | Iva  | Ala  | Arg | Lys | Asn-Gln-NH$_2$ |
| 20 | Phe  | CH$_2$—O  | (pF)Phe   | Iva  | Ala  | Arg | Lys | Asn-Gln-NH$_2$ |
| 21 | Nphe | CO—NH     | Phe       | Iva  | Ala  | Arg | Lys | —NH$_2$ |
| 22 | Phe  | CO—NH     | (pF)Phe   | Iva  | Ala  | Arg | Lys | —NH$_2$ |
| 23 | Phe  | CH$_2$—NH | (pF)Phe   | Iva  | Ala  | Arg | Lys | —NH$_2$ |
| 24 | Phe  | CH$_2$—O  | (pF)Phe   | Iva  | Ala  | Arg | Lys | —NH$_2$ |
| 25 | Nphe | CO—NH     | Phe       | Iva  | Aib  | Arg | Lys | Asn-Gln-NH$_2$ |
| 26 | Phe  | CO—NH     | (pF)Phe   | Iva  | Aib  | Arg | Lys | Asn-Gln-NH$_2$ |
| 27 | Phe  | CH$_2$—NH | (pF)Phe   | Iva  | Aib  | Arg | Lys | Asn-Gln-NH$_2$ |
| 28 | Phe  | CH$_2$—O  | (pF)Phe   | Iva  | Aib  | Arg | Lys | Asn-Gln-NH$_2$ |
| 29 | Nphe | CO—NH     | Phe       | Iva  | Aib  | Arg | Lys | —NH$_2$ |
| 30 | Phe  | CO—NH     | (pF)Phe   | Iva  | Aib  | Arg | Lys | —NH$_2$ |
| 31 | Phe  | CH$_2$—NH | (pF)Phe   | Iva  | Aib  | Arg | Lys | —NH$_2$ |
| 32 | Phe  | CH$_2$—O  | (pF)Phe   | Iva  | Aib  | Arg | Lys | —NH$_2$ |
| 33 | Nphe | CO—NH     | Phe       | Aib  | Iva  | Arg | Lys | Asn-Gln-NH$_2$ |
| 34 | Phe  | CO—NH     | (pF)Phe   | Aib  | Iva  | Arg | Lys | Asn-Gln-NH$_2$ |
| 35 | Phe  | CH$_2$—NH | (pF)Phe   | Aib  | Iva  | Arg | Lys | Asn-Gln-NH$_2$ |
| 36 | Phe  | CH$_2$—O  | (pF)Phe   | Aib  | Iva  | Arg | Lys | Asn-Gln-NH$_2$ |
| 37 | Nphe | CO—NH     | Phe       | Aib  | Iva  | Arg | Lys | —NH$_2$ |
| 38 | Phe  | CO—NH     | (pF)Phe   | Aib  | Iva  | Arg | Lys | —NH$_2$ |
| 39 | Phe  | CH$_2$—NH | (pF)Phe   | Aib  | Iva  | Arg | Lys | —NH$_2$ |
| 40 | Phe  | CH$_2$—O  | (pF)Phe   | Aib  | Iva  | Arg | Lys | —NH$_2$ |
| 41 | Nphe | CO—NH     | Phe       | Aib  | Ala  | Arg | Lys | Asn-Gln-NH$_2$ |
| 42 | Phe  | CO—NH     | (pNO$_2$)Phe | Aib | Ala | Arg | Lys | Asn-Gln-NH$_2$ |
| 43 | Phe  | CH$_2$—NH | (pNO$_2$)Phe | Aib | Ala | Arg | Lys | Asn-Gln-NH$_2$ |
| 44 | Phe  | CH$_2$—O  | (pNO$_2$)Phe | Aib | Ala | Arg | Lys | Asn-Gln-NH$_2$ |
| 45 | Nphe | CO—NH     | Phe       | Aib  | Ala  | Arg | Lys | —NH$_2$ |
| 46 | Phe  | CO—NH     | (pNO$_2$)Phe | Aib | Ala | Arg | Lys | —NH$_2$ |

-continued

| | Xaa¹ | ? | Xbb⁴ | Xcc⁷ | Xdd¹¹ | Xee¹⁴ | Xff¹⁵ | R |
|---|---|---|---|---|---|---|---|---|
| 47 | Phe | CH₂—NH | (pNO₂)Phe | Aib | Ala | Arg | Lys | —NH₂ |
| 48 | Phe | CH₂—O | (pNO₂)Phe | Aib | Ala | Arg | Lys | —NH₂ |
| 49 | Nphe | CO—NH | Phe | Aib | Aib | Arg | Lys | Asn-Gln-NH₂ |
| 50 | Phe | CO—NH | (pNO₂)Phe | Aib | Aib | Arg | Lys | Asn-Gln-NH₂ |
| 51 | Phe | CH₂—NH | (pNO₂)Phe | Aib | Aib | Arg | Lys | Asn-Gln-NH₂ |
| 52 | Phe | CH₂—O | (pNO₂)Phe | Aib | Aib | Arg | Lys | Asn-Gln-NH₂ |
| 53 | Nphe | CO—NH | Phe | Aib | Aib | Arg | Lys | —NH₂ |
| 54 | Phe | CO—NH | (pNO₂)Phe | Aib | Aib | Arg | Lys | —NH₂ |
| 55 | Phe | CH₂—NH | (pNO₂)Phe | Aib | Aib | Arg | Lys | —NH₂ |
| 56 | Phe | CH₂—O | (pNO₂)Phe | Aib | Aib | Arg | Lys | —NH₂ |
| 57 | Nphe | CO—NH | Phe | Iva | Ala | Arg | Lys | Asn-Gln-NH₂ |
| 58 | Phe | CO—NH | (pNO₂)Phe | Iva | Ala | Arg | Lys | Asn-Gln-NH₂ |
| 59 | Phe | CH₂—NH | (pNO₂)Phe | Iva | Ala | Arg | Lys | Asn-Gln-NH₂ |
| 60 | Phe | CH₂—O | (pNO₂)Phe | Iva | Ala | Arg | Lys | Asn-Gln-NH₂ |
| 61 | Nphe | CO—NH | Phe | Iva | Ala | Arg | Lys | —NH₂ |
| 62 | Phe | CO—NH | (pNO₂)Phe | Iva | Ala | Arg | Lys | —NH₂ |
| 63 | Phe | CH₂—NH | (pNO₂)Phe | Iva | Ala | Arg | Lys | —NH₂ |
| 64 | Phe | CH₂—O | (pNO₂)Phe | Iva | Ala | Arg | Lys | —NH₂ |
| 65 | Nphe | CO—NH | Phe | Iva | Aib | Arg | Lys | Asn-Gln-NH₂ |
| 66 | Phe | CO—NH | (pNO₂)Phe | Iva | Aib | Arg | Lys | Asn-Gln-NH₂ |
| 67 | Phe | CH₂—NH | (pNO₂)Phe | Iva | Aib | Arg | Lys | Asn-Gln-NH₂ |
| 68 | Phe | CH₂—O | (pNO₂)Phe | Iva | Aib | Arg | Lys | Asn-Gln-NH₂ |
| 69 | Nphe | CO—NH | Phe | Iva | Aib | Arg | Lys | —NH₂ |
| 70 | Phe | CO—NH | (pNO₂)Phe | Iva | Aib | Arg | Lys | —NH₂ |
| 71 | Phe | CH₂—NH | (pNO₂)Phe | Iva | Aib | Arg | Lys | —NH₂ |
| 72 | Phe | CH₂—O | (pNO₂)Phe | Iva | Aib | Arg | Lys | —NH₂ |
| 73 | Nphe | CO—NH | Phe | Aib | Iva | Arg | Lys | Asn-Gln-NH₂ |
| 74 | Phe | CO—NH | (pNO₂)Phe | Aib | Iva | Arg | Lys | Asn-Gln-NH₂ |
| 75 | Phe | CH₂—NH | (pNO₂)Phe | Aib | Iva | Arg | Lys | Asn-Gln-NH₂ |
| 76 | Phe | CH₂—O | (pNO₂)Phe | Aib | Iva | Arg | Lys | Asn-Gln-NH₂ |
| 77 | Nphe | CO—NH | Phe | Aib | Iva | Arg | Lys | —NH₂ |
| 78 | Phe | CO—NH | (pNO₂)Phe | Aib | Iva | Arg | Lys | —NH₂ |
| 79 | Phe | CH₂—NH | (pNO₂)Phe | Aib | Iva | Arg | Lys | —NH₂ |
| 80 | Phe | CH₂—O | (pNO₂)Phe | Aib | Iva | Arg | Lys | —NH₂ |

Among these, even more preferred are compounds in which ? is CO—NH or CH₂—NH or CH₂—O; Xaa¹ is Phe or Nphe; Xbb⁴ is Phe or (pF)Phe or (pNO₂)Phe; Xcc⁷ and Xdd¹¹ are Ala; 2-amino-2-methyl-propionic acid (Aib); 2-amino-2-methyl-butyric acid (Iva); Xee¹⁴ is Arg; Xff¹⁵ is Lys; R is Asn-Gln-NH₂ or —NH₂.
represented by the following formulas:

a)
H-Nphe-Gly-Gly-Phe-Thr-Gly-Aib-Arg-Lys-Ser-Ala-Arg-Lys-Arg-Lys-Asn-Gln-NH₂ b)
H-Phe-Gly-Gly-(pF)Phe-Thr-Gly-Aib-Arg-Lys-Ser-Ala-Arg-Lys-Arg-Lys-Asn-Gln-NH₂ c)
H-Phe-?(CH₂—NH)-Gly-Gly-(pF)Phe-Thr-Gly-Aib-Arg-Lys-Ser-Ala-Arg-Lys-Arg-Lys-Asn-Gln-NH₂ d)
H-Phe-?(CH₂—O)-Gly-Gly-(pF)Phe-Thr-Gly-Aib-Arg-Lys-Ser-Ala-Arg-Lys-Arg-Lys-Asn-Gln-NH₂ e)
H-Phe-Gly-Gly-(pNO₂)Phe-Thr-Gly-Aib-Arg-Lys-Ser-Ala-Arg-Lys-Arg-Lys-Asn-Gln-NH₂ f)
H-Phe-?(CH₂—NH)-Gly-Gly-(pNO₂)Phe-Thr-Gly-Aib-Arg-Lys-Ser-Ala-Arg-Lys-Arg-Lys-Asn-Gln-NH₂ g)
H-Phe-?(CH₂—O)-Gly-Gly-(pNO₂)Phe-Thr-Gly-Aib-Arg-Lys-Ser-Ala-Arg-Lys-Arg-Lys-Asn-Gln-NH₂ h)
H-Nphe-Gly-Gly-Phe-Thr-Gly-Aib-Arg-Lys-Ser-Ala-Arg-Lys-Arg-Lys-NH₂ i)
H-Phe-Gly-Gly-(pF)Phe-Thr-Gly-Aib-Arg-Lys-Ser-Ala-Arg-Lys-Arg-Lys-NH₂ l)
H-Phe-?(CH₂—NH)-Gly-Gly-(pF)Phe-Thr-Gly-Aib-Arg-Lys-Ser-Ala-Arg-Lys-Arg-Lys-NH₂ m)
H-Phe-?(CH₂—O)-Gly-Gly-(pF)Phe-Thr-Gly-Aib-Arg-Lys-Ser-Ala-Arg-Lys-Arg-Lys-NH₂ n)
H-Phe-Gly-Gly-(pNO₂)Phe-Thr-Gly-Aib-Arg-Lys-Ser-Ala-Arg-Lys-Arg-Lys-NH₂ o)
H-Phe-?(CH₂—NH)-Gly-Gly-(pNO₂)Phe-Thr-Gly-Aib-Arg-Lys-Ser-Ala-Arg-Lys-Arg-Lys-NH₂ p)
H-Phe-?(CH₂—O)-Gly-Gly-(pNO₂)Phe-Thr-Gly-Aib-Arg-Lys-Ser-Ala-Arg-Lys-Arg-Lys-NH₂ aa)
H-Nphe-Gly-Gly-Phe-Thr-Gly-Aib-Arg-Lys-Ser-Aib-Arg-Lys-Arg-Lys-Asn-Gln-NH₂ bb)
H-Phe-Gly-Gly-(pF)Phe-Thr-Gly-Aib-Arg-Lys-Ser-Aib-Arg-Lys-Arg-Lys-Asn-Gln-NH₂ cc)
H-Phe-?(CH₂—NH)-Gly-Gly-(pF)Phe-Thr-Gly-Aib-Arg-Lys-Ser-Aib-Arg-Lys-Arg-Lys-Asn-Gln-NH₂ dd)
H-Phe-?(CH$_2$—O)-Gly-Gly-(pF)Phe-Thr-Gly-Aib-Arg-Lys-Ser-Aib-Arg-Lys-Arg-Lys-Asn-Gln-NH$_2$ ee)
H-Phe-Gly-Gly-(pNO$_2$)Phe-Thr-Gly-Aib-Arg-Lys-Ser-Aib-Arg-Lys-Arg-Lys-Asn-Gln-NH$_2$ ff)
H-Phe-?(CH$_2$—NH)-Gly-Gly-(pNO$_2$)Phe-Thr-Gly-Aib-Arg-Lys-Ser-Aib-Arg-Lys-Arg-Lys-Asn-Gln-NH$_2$ gg)
H-Phe-?(CH$_2$—O)-Gly-Gly-(pNO$_2$)Phe-Thr-Gly-Aib-Arg-Lys-Ser-Aib-Arg-Lys-Arg-Lys-Asn-Gln-NH$_2$ hh)
H-Nphe-Gly-Gly-Phe-Thr-Gly-Aib-Arg-Lys-Ser-Aib-Arg-Lys-Arg-Lys-NH$_2$ ii)
H-Phe-Gly-Gly-(pF)Phe-Thr-Gly-Aib-Arg-Lys-Ser-Aib-Arg-Lys-Arg-Lys-NH$_2$ ll)
H-Phe-?(CH$_2$—NH)-Gly-Gly-(pF)Phe-Thr-Gly-Aib-Arg-Lys-Ser-Aib-Arg-Lys-Arg-Lys-NH$_2$ mm)
H-Phe-?(CH$_2$—O)-Gly-Gly-(pF)Phe-Thr-Gly-Aib-Arg-Lys-Ser-Aib-Arg-Lys-Arg-Lys-NH$_2$ nn)
H-Phe-Gly-Gly-(pNO$_2$)Phe-Thr-Gly-Aib-Arg-Lys-Ser-Aib-Arg-Lys-Arg-Lys-NH$_2$ oo)
H-Phe-?(CH$_2$—NH)-Gly-Gly-(pNO$_2$)Phe-Thr-Gly-Aib-Arg-Lys-Ser-Aib-Arg-Lys-Arg-Lys-NH$_2$ pp)
H-Phe-?(CH$_2$—O)-Gly-Gly-(pNO$_2$)Phe-Thr-Gly-Aib-Arg-Lys-Ser-Aib-Arg-Lys-Arg-Lys-NH$_2$ aaa)
H-Nphe-Gly-Gly-Phe-Thr-Gly-Aib-Arg-Lys-Ser-Iva-Arg-Lys-Arg-Lys-Asn-Gln-NH$_2$ bbb)
H-Phe-Gly-Gly-(pF)Phe-Thr-Gly-Aib-Arg-Lys-Ser-Iva-Arg-Lys-Arg-Lys-Asn-Gln-NH$_2$ ccc)
H-Phe-?(CH$_2$—NH)-Gly-Gly-(pF)Phe-Thr-Gly-Aib-Arg-Lys-Ser-Iva-Arg-Lys-Arg-Lys-Asn-Gln-NH$_2$ ddd)
H-Phe-?(CH$_2$—O)-Gly-Gly-(pF)Phe-Thr-Gly-Aib-Arg-Lys-Ser-Iva-Arg-Lys-Arg-Lys-Asn-Gln-NH$_2$ eee)
H-Phe-Gly-Gly-(pNO$_2$)Phe-Thr-Gly-Aib-Arg-Lys-Ser-Iva-Arg-Lys-Arg-Lys-Asn-Gln-NH$_2$ fff)
H-Phe-?(CH$_2$—NH)-Gly-Gly-(pNO$_2$)Phe-Thr-Gly-Aib-Arg-Lys-Ser-Iva-Arg-Lys-Arg-Lys-Asn-Gln-NH$_2$ ggg)
H-Phe-?(CH$_2$—O)-Gly-Gly-(pNO$_2$)Phe-Thr-Gly-Aib-Arg-Lys-Ser-Iva-Arg-Lys-Arg-Lys-Asn-Gln-NH$_2$ hhh)
H-Nphe-Gly-Gly-Phe-Thr-Gly-Aib-Arg-Lys-Ser-Iva-Arg-Lys-Arg-Lys-NH$_2$ iii)
H-Phe-Gly-Gly-(pF)Phe-Thr-Gly-Aib-Arg-Lys-Ser-Iva-Arg-Lys-Arg-Lys-NH$_2$ lll)
H-Phe-?(CH$_2$—NH)-Gly-Gly-(pF)Phe-Thr-Gly-Aib-Arg-Lys-Ser-Iva-Arg-Lys-Arg-Lys-NH$_2$ mmm)
H-Phe-?(CH$_2$—O)-Gly-Gly-(pF)Phe-Thr-Gly-Aib-Arg-Lys-Ser-Iva-Arg-Lys-Arg-Lys-NH$_2$ nnn)
H-Phe-Gly-Gly-(pNO$_2$)Phe-Thr-Gly-Aib-Arg-Lys-Ser-Iva-Arg-Lys-Arg-Lys-NH$_2$ ooo)
H-Phe-?(CH$_2$—NH)-Gly-Gly-(pNO$_2$)Phe-Thr-Gly-Aib-Arg-Lys-Ser-Iva-Arg-Lys-Arg-Lys-NH$_2$ ppp)
H-Phe-?(CH$_2$—O)-Gly-Gly-(pNO$_2$)Phe-Thr-Gly-Aib-Arg-Lys-Ser-Iva-Arg-Lys-Arg-Lys-NH$_2$ Peptide analogs according to the invention can be synthesized by different techniques known in the literature, for example Schroeder et al. "The Peptides" vol 1, Academic Press, 1965; Bodanszky et al. "Peptide Synthesis" Interscience Publisher, 1966; Barany & Merrifield, "The peptides; Analysis, Synthesis, Biology", 2, Academic Press, 1980; E. Atheron e R. C. Sheppard, "Solid Phase Peptide Synthesis" IRL Press at Oxford University Press 1989; J. Jones, "The Chemical Synthesis of Peptides", Claredon Press, Oxford 1994. These techniques include solid phase peptide synthesis or solution phase peptide synthesis, synthetic methods of organic chemistry, or any combination of the above. The choice of the synthesis scheme will obviously depend on the composition of a given peptide. Preferably, synthetic methods are employed that are based on appropriate combinations of solid phase techniques and classical solution phase methods, involving low production costs, particularly on an industrial scale. In detail, said methods comprise:

i) Synthesis in solution of peptide chain fragments through sequential coupling of N-protected amino acids, suitably activated, to an amino acid or a C-protected peptide chain, with isolation of the intermediates, subsequent selective deprotection of N and C-terminal ends of said fragments, and their repeated coupling until the desired peptide is obtained. Where necessary, side chains are deprotected.

ii) Solid phase synthesis of the peptide chain from the C-terminal end toward the N-terminal end on an insoluble polymeric support. The peptide is removed from the resin by hydrolysis with anhydrous fluoridric acid or trifluoroacetic acid, with simultaneous deprotection of the side chains.

At the end of the synthesis, peptides can be purified and isolated by treatment with suitable solvents and by chromatographic techniques, such as HPLC. The peptide analogs according to the invention act on the NOP receptor as i) full agonists, when they present the structure [Phe$^1$?(CO—NH)Gly$^2$], ii) partial agonists, when they present the structure [Phe$^1$?(CH$_2$—NH)Gly$^2$] or [Phe$^1$?(CH$_2$—O)Gly$^2$], and as pure antagonists, when they present the structure [Nphe$^1$?(CO—NH)Gly$^2$].

In addition, the present invention relates to pharmaceutical compositions containing the peptide analogs described here, possibly in combination with pharmaceutically acceptable vehicles and excipients. The compositions of the invention can be administered through the oral or parenteral route, or through the respiratory, rectal, spinal, intrathecal, intravesical or topical route, as injectable preparation, capsule, tablet, granulate, solution, suspension, syrup, suppository, nasal spray, cream, ointment, gel, controlled release preparation or other. The principles and the methods for preparation of pharmaceutical composition are well known to the experts in the field and are described, for instance, in Remington's Pharmaceutical Sciences, 18° Edition, Mack Publishing Company, Easton, Pa., 1990. Pharmaceutical compositions according to the invention will contain an effective amount of peptides (or of their derivatives) generally ranging between 0.001 and 100 mg, preferably between 0.01 and 10 mg. The daily dose will vary depending on the type of pathology/dysfunction, age, sex and patient's body weight, the general health status and other variables which need to be evaluated on a cases by case basis.

Considering the activity profile shown by the peptides of the invention in biological tests, the pharmaceutical compositions containing said peptides can be used for treatment of dysfunctions, conditions or pathological states, comprising neurological and neuro-sensory dysfunctions. It is desirable to obtain a potent and prolonged NOP receptor activation for the treatment of anxiety, anorexia, hypertension, tachycardia, water retention disorders, hyponatremia, congestive heart failure, smooth muscle motor dysfunctions in gastrointestinal, respiratory, and genitourinary tracts (especially urinary incontinence following neurogenic bladder), inflammatory states, or peripheral or spinal analgesia, particularly for the treatment of chronic pain, or, even more, in cough control. Moreover, it will be possible to use the antagonists for treatment of memory, mood, locomotor activity (e.g. Parkinson's disease), food intake disorders (e.g. bulimia), or, more in general, for treatment of obese patients. The high molecular weight of these compounds, and the presence within them of residues that can be positively charged at physiological pH make it unlikely that they can cross the blood-brain barrier. Said compounds can exert central effects following local administration, even though they show predominantly a peripheral distribution. For instance, agonist compounds can induce analgesia at the level of the central nervous system, following intrathecal or spinal administration.

EXPERIMENTAL PART

1. Peptide Synthesis
1.1 General Scheme of Synthesis

The peptides of the invention were prepared by solid phase synthesis using a resin 4-(2',4'-dimethoxyphenyl-Fmoc-aminomethylphenoxyacetamido-norleucyl-resin (Rink-Amide MBHA resin). Fmoc amino acids fluoremylmethoxycarbonyl) have been condensed using [O-(7-azabenzotriazol-1-yl)-1,1,3,3-tetramethyluroniumexafluorophosphate] (HATU) as reagent for activation of the carboxylic function. Fmoc groups have been removed by use of 20% piperidine in DMF (dimethylformamide) and the resin bound to the protected peptide has been treated with the K reagent in order to obtain the raw peptide. Compounds containing a modified peptide bond between the first two amino acid residues [Phe$^1$?(CH$_2$—NH)Gly$^2$] or [Phe$^1$?(CH$_2$—O)Gly$^2$] have been obtained by condensation of Boc-Phe-CHO on the protected peptide (2-17) or (2-16) or (2-15) bound to the resin during the last synthesis step, thus reducing in situ the intermediate "imino" derivative with NaBH$_3$CN, or condensing the fragment Boc-[Phe$^1$?(CH$_2$—O)Gly$^2$]-OH (that was obtained following the methods reported in the literature: Balboni et al. *J. Chem. Soc. Perkin Trans I*, 1998, pg 1645-1651) on the protected peptide (3-17) or (3-16) or (3-15) bound to the resin during the last synthesis step, using HATU as condensing agent.

The analytical control of both raw and final products was done by analytical HPLC in the Beckmann System Gold 168, using a Alltech C-18 column (150×4.6 mm, 5 µm). Compounds were analysed using a binary eluting system composed of solvent A: 35 mM NaH$_2$PO$_4$ (pH 2.1) and solvent B: 59 mM NaH$_2$PO$_4$ (pH 2.1)-acetonitrile (60:40 v/v), programming the gradient according to the physico-chemical properties of the compounds to be analysed, at a flow rate of 1 mL/min and at a wave length of 220 nm. The raw peptide has been purified by use of the a Water preparative HPLC Delta Prep 4000 system, using a Water radial packing column Delta-LC 40 mm (30×40 cm, C18, 300 A, 15 µm) that was eluted with the same mobile phase used for analytical HPLC and with a gradient programmed according to the analytical profile of the raw reaction products. The molecular weight of the final compound was obtained by electro-spray mass spectrometry using the instrument micromass ZMD2000.

For the intermediates of some peptides, a spectroscopic 1HNMR analysis was performed using a Bruker 200 MHz instrument.

1.2 Procedure.

Peptide analogs b), c) and d) described above were prepared according to the procedures described here below.

The resin Rink-Amide MBHA (0.65 mmol/g, 0.2 g) was treated with piperidine (20%) in DMF and condensed with Fmoc-Gln(Trt)-OH, activating the carboxylic function with HATU. The following Fmoc amino acids were coupled sequentially to the elongating peptide chain: Fmoc-Asn(Trt)-OH, Fmoc-Lys(Boc)-OH, Fmoc-Arg(Pmc)-OH, Fmoc-Lys(Boc)-OH, Fmoc-Arg(Pmc)-OH, Fmoc-Ala-OH, Fmoc-Ser(tBu)-OH, Fmoc-Lys(Boc)-OH, Fmoc-Arg(Pmc)-OH, Fmoc-Aib-OH, Fmoc-Gly-OH, Fmoc-Thr(tBu)-OH, Fmoc-(pF)Phe-OH, Fmoc-Gly-OH, Fmoc-Gly-OH, Fmoc-Phe-OH. All Fmoc amino acids (4 equivalents) were coupled to the elongating peptide chain using HATU (4 equivalents) and diisopropylethylamine (4 equivalents) in DMF; the coupling reaction was performed for one hour. In order to optimize the synthesis yield, and make purification of the compounds easier, double coupling with one hour acylation time was necessary for the Aib residue. Piperidine (20%) in DMF was used to remove Fmoc groups in each step. Following deprotection of the last $N^\alpha$-Fmoc group, the peptide resin was washed with methanol and dried under vacuum to yield [(pF)Phe$^4$,Aib$^7$,Arg$^{14}$,Lys$^{15}$]-N/OFQ(1-17)-Rink-Amide MBHA-Protected resin. This protected peptide resin was treated with the K reagent (TFA/H$_2$O/phenol/ethanedithiol/thioanisole 82.5:5:5:2.5:5; v/v; 10 mL/0.2 g resin) for 1 h at room temperature. After filtering the exhausted resin, the solvent was concentrated under vacuum and the residue was ground in ether. The raw peptide was purified by preparative reverse phase HPLC, and a white powder was obtained following lyophilization.

The synthesis of [Phe$^1$?(CH$_2$—NH)Gly$^2$,(pF)Phe$^4$,Aib$^7$, Arg$^{14}$,Lys$^{15}$]-N/OFQ-NH$_2$ (peptide c) was made starting from the intermediate [(pF)Phe$^4$,Aib$^7$Arg$^{14}$,Lys$^{15}$]-N/OFQ-(2-17)-resin synthesized as described above. This intermediate (0.2 g, 0.65 mmol/g, 0.13 mmol) was resuspended and swollen in methanol containing 1% (V/V) acetic acid (2 mL). After 20 minutes, a solution containing Boc-Phe-CHO (0.065 g, 0.26 mmol) and NaBH3CN (0.033 g, 0.52 mmol) solubilized in methanol (0.8 mL) was added, and the reaction mixture was stirred for 1.5 h. The resin was then washed with methanol and treated with reagent K as described above. The synthesis of [Phe$^1$?(CH$_2$—O)Gly$^2$,(pF)Phe$^4$,Aib$^7$,Arg$^{14}$, Lys$^{15}$]N/OFQ-NH$_2$ (peptide d) was made starting from the intermediate [(pF)Phe$^4$,Aib$^7$Arg$^{14}$,Lys$^{15}$]-N/OFQ(3-17)-resin synthesized as described above. This intermediate (0.2 g, 0.65 mmol/g, 0.13 mmol) was acylated at the last step with Boc-Phe[?(CH$_2$—O)]Gly-OH (4 equivalents, 0.16 g, 0.52 mmol) activating the carboxylic function with HATU under the same conditions described for the normal acylation steps.

112), [Phe$^1$?(CH$_2$—NH)Gly$^2$,(pF)Phe$^4$,Aib$^7$Arg$^{14}$,Lys$^{15}$]N/OFQ-NH$_2$ (UFP-113), [Nphe$^1$,Aib$^7$Arg$^{14}$,Lys$^{15}$]N/OFQ-NH$_2$ (UFP-111), and with the reference peptide N/OFQ.

TABLE 1

Biological activity of [(pF)Phe$^4$,Aib$^7$,Arg$^{14}$,Lys$^{15}$]N/OFQ-NH$_2$ (UFP-112), [Phe$^1$?(CH$_2$—NH)Gly$^2$,(pF)Phe$^4$,Aib$^7$,Arg$^{14}$,Lys$^{15}$]N/OFQ-NH$_2$ (UFP-113), [Nphe$^1$,Aib$^7$,Arg$^{14}$,Lys$^{15}$]N/OFQ-NH$_2$ (UFP-111), and the reference peptide N/OFQ.

|  | Receptor binding | Membrane of CHO$_{hNOP}$cells Stimulation upon binding GTP?S | | | Mouse vas deferens Inhibition of the twitch induced by electric stimulation | | |
|---|---|---|---|---|---|---|---|
|  |  | Agonist | | Antagonist | Agonist | | Antagonist |
|  | pK$_i$ | pEC$_{50}$ | E$_{max}$ | pA$_2$ | pEC$_{50}$ | E$_{max}$ | pA$_2$ |
| N/OFQ | 9.50 | 9.04 | 100 ± 9% | ND | 7.39 | −84 ± 3% | ND |
| UFP-112 | 10.55 | 10.55 | 118 ± 9% | ND | 9.48 | −85 ± 2% | ND |
| UFP-113 | 10.26 | 9.72 | 79 ± 3% | ND | Variable agonist effects | | 9.28 |
| UFP-111 | 9.75 | Inactive | | 8.68 | Inactive | | 7.46 |

The results are the average (median) of 4-6 determinations. ND: not determinable because the compound presents agonist effects.

Subsequently, the resin was washed with methanol and treated with reagent K as described above 2. Pharmacological Tests.

2.1 Materials and Methods

The compounds were tested in vitro on Hamster oocytes membranes expressing the human recombinant NOP receptor (CHO$_{hNoP}$) (receptor binding experiments and GTP?S binding stimulation experiments) and on the mouse vas deferens after electrical stimulation. The conditions used to study the effects of the compounds in bioassay experiments (mouse vas deferens) are described in Bigoni et al. (*Naunyn Schmiedebergs Arch Pharmacol* 359, 160-7, 1999), while the conditions used to study the effects in CHO$_{hNOP}$ cells are described in Mc Donald et al. (*Naunyn Schmiedebergs Arch Pharmacol*, 367, 183-187, 2003). In each series of experiments, the activity of new compounds was compared to that of the natural N/OFQ peptide.

2.2 Results.

In receptor binding experiments, all compounds tested proved capable of displacing completely the tritiated N/OFQ from the human recombinant NOP receptor. Compounds exhibited very different receptor affinities (pK$_i$) depending on the various chemical modifications. In general, compounds with structure [Phe$^1$?(CO—NH)Gly$^2$] showed higher affinity than those having the structure [Phe$^1$?(CH$_2$—NH)Gly$^2$] and extremely higher affinity than those having the structure [Nphe$^1$?(CO—NH)Gly$^2$]. Furthermore the compounds having the combined modifications [(pF)Phe$^4$,Aib$^7$,Arg$^{14}$,Lys$^{15}$] showed greater affinity than those having single modifications.

In the functional tests involving stimulation of GTP?S binding and in the tests involving inhibition of the twitch induced by electrical stimulation of the mouse vas deferens, compounds having the structure [Phe$^1$?(CO—NH)Gly$^2$] mimicked the effects of N/OFQ, and in particular induced similar maximal effects, therefore acting as full agonists, while compounds having the structure [Phe$^1$?(CH$_2$—NH)Gly$^2$] acted as partial agonists since their maximal effects were lower than with N/OFQ. At last, compounds having the structure [Nphe$^1$?(CO—NH)Gly$^2$] did not produce any effect per se but acted as competitive antagonists of N/OFQ.

To simplify, Table 1 reports the results obtained with the compounds [(pF)Phe$^4$,Aib$^7$Arg$^{14}$,Lys$^{15}$]N/OFQ-NH$_2$ (UFP- As it is highlighted in Table 1, the compound UFP-113 behaves as partial NOP receptor agonist, evoking maximal effects that are lower than N/OFQ, both in the GTP?S assay and in the inhibition assay of contraction induced by electrical stimulation of mouse vas deferens. UFP-111 proved to be a pure and potent antagonist selective for the NOP receptor. The analysis by Schild (performed in both GTP?S experiments and with the mouse vas deferens system) indicates that the compound behaves as competitive antagonist of NOP receptor with potency values (expressed as pA$_2$) of 8.68 and 7.46, respectively (see Table 1).

2.3. Selectivity of the UFP-112 Compound.

UFP-112 effects are mediated by NOP receptor activation, as shown by the fact that the action of this peptide in the mouse vas deferens was not modified in presence of naloxone (a non-selective antagonist of classical opioid receptors, but not of the NOP receptor) but turned out to be effectively antagonized by UFP-101 which is a selective NOP receptor antagonist ([Nphe1,Arg14,Lys15]N/OFQ-NH$_2$, Calò et al., *Br J Pharmacol* 136, 303-311, 2002). UFP-101 used in competition with UFP-112 showed a potency value (pA$_2$ 6.81) similar to that obtained when it is used in competition with the endogenous agonist N/OFQ (pA$_2$ 6.91). This shows that the three molecules (N/OFQ, UFP-112 e UFP-101) interact with the same receptor: the NOP receptor. This is further shown by the results obtained with tissues from knock-out mice (Ref. Nishi, M. et al., *Unrestrained nociceptive response and disregulation of hearing ability in mice lacking the nociceptin/orphaninFQ receptor*. Embo J 16 (8): 1858-64, 1997) for the NOP receptor gene (NOP$^{-/-}$) (see Table 2).

TABLE 2 effects of the agonist N/OFQ and UFP112 and of the agonist DOP, D-Pen2,D-Pen5enkephalin (DPDPE), on the vas deferens of wild type (NOP$^{+/+}$) and knockout mice for the NOP receptor (NOP$^{-/-}$).

|  | NOP$^{+/+}$ | | NOP$^{-/-}$ | |
|---|---|---|---|---|
| Compound | pEC$_{50}$ | E$_{max}$ | pEC$_{50}$ | E$_{max}$ |
| N/OFQ | 7.47 | 84 ± 4% | <6 | — |
| UFP-112 | 8.94 | 93 ± 3% | <6 | — |
| DPDPE | 8.40 | 93 ± 3% | 8.20 | 91 ± 5% |

The inhibitory effect on the contraction induced by electrical stimulation, evoked by UFP-112 (similar to what is found with N/OFQ) disappeared in the vas deferens isolated from NOP$^{-/-}$ mice, confirming that the biological actions of UFP-112 are only due to the interaction with the NOP receptor.

The compound [D-Pen$^2$,D-Pen$^5$]-Enkephalin, DPDPE (Ref. Life Sci. 1983; 33 Suppl 1:447-50), a selective DOP agonist, was used as the positive control. This control shows which are the tissues derived from NOP receptor knockout mice that respond normally to inhibitory stimuli that do not use the NOP receptor.

2.4 Pharmacological Tests on Selectivity of the Compounds According to the Invention The compounds have been tested in vitro on membranes of Hamster oocytes (CHO) expressing the human recombinant NOP receptor (CHO$_{hNOP}$), as in paragraph 2.1, according to Mc Donald et al. (*Naunyn Schmiedebergs Arch Pharmacol* 367, 183-187, 2003).

The studies on selectivity of these compounds for the NOP receptor were performed by receptor binding studies on membranes of CHO cells transfected with human recombinant opioid receptors of mu (MOP), delta (DOP) and kappa (KOP) type, using the same method as for CHO$_{hNOP}$. Selectivity studies were performed by competition experiments according to the methods described in Mc Donald et al. (*Naunyn Schmiedebergs Arch Pharmacol* 367, 183-187, 2003). To measure the pK$_i$ for N/OFQ, tritiated N/OFQ was used as radioligand, whereas [$^3$H]-Diprenorphine was used for the classical opioid receptors. The activity of the new compounds was compared to that of the natural peptide N/OFQ.

In receptor binding experiments, performed on membranes of transfected CHO cells, UFP-111, UFP-112 and UFP-113 showed a higher selectivity (>100 fold) for the NOP receptor than MOP, KOP and DOP receptors (see Table 3).

TABLE 3

Affinity (pK$_i$) of UFP-112, UFP-113 and UFP-111 for the NOP, MOP, DOP and KOP receptors transfected in CHO cells (Ref. Mc Donald et al. (Naunyn Schmiedebergs Arch Pharmacol 367, 183-187, 2003).

| Receptors | pK$_i$ | | | |
|---|---|---|---|---|
| (standard ligands used per receptor) | NOP (N/OFQ)[1] | MOP (DAMGO)[2,3] | DOP (Naltrindole)[3] | KOP (Nor-BNI)[3] |
| Standard ligands | 9.50 | 8.43 | 9.97 | 9.90 |
| UFP-112 | 10.55 | 7.13 | 6.37 | 8.36 |
| UFP-113 | 10.26 | 6.45 | 5.69 | 7.55 |
| UFP-111 | 7.75 | <5.0 | <5.0 | 6.17 |

Data are the mean of 4 experiments.
Note[1]- The tritiated ligand used is [$^3$H]N/OFQ
Note[2]- DAMGO means [D-Ala(2),N-MePhe(4),Gly-ol(5)]enkephalin
Note[3]- The tritiated ligand used is [$^3$H]-Diprenorphine 3. In Vivo Studies on the Efficacy of the Full Agonist Compound UFP-112

The compound UFP-112; that is a full agonist, was tested in vivo in mice, in different assays:
1) tail withdrawal assay, according to the experimental protocols described by Calò et al., (*Br J Pharmacol* 125, 373-378, 1998) and Rizzi et al. (*Clin Pharmacol* 18, 56, 2004);
2) measurement of food intake in fed animals, as described by Rizzi et al. (National Congress of the Italian Society of Neuroscience and joint Italian-Swedish Neuroscience Meetings, Ischia (Napoli) 1-4 Oct. 2005);
3) assay for measurement of spontaneous locomotor activity, as described by Rizzi et al., (*Naunyn Schmiedebergs Arch Pharmacol* 363, 161-165, 2001.

In each assay, UFP-112 and N/OFQ activities were measured as equi-effective doses. As UFP-112 shows about 100-fold higher potency, peptide UFP-112 was used at doses comprising between 0.001 and 0.1 nmol and N/OFQ was used at doses comprising between 0.1 and 10 nmol.

In the analgesiometric tail withdrawal test in mice, UFP-112 at equi-effective doses mimicked the effects of the natural ligand N/OFQ, although it showed its action for a longer period (>120 minutes).

UFP-112, in the dose range between 0.001-0.1 nmol, induces pronociceptive effects, if injected via the intracerebroventricular (i.c.v.) route, whereas it evoked antinociceptive effects when it was administered intrathecally (i.t.) (see FIG. 1). Said effects (similar to what is found with N/OFQ) are mediated by NOP receptor activation because they are absent in NOP$^{-/-}$ mice.

N/OFQ and UFP-112 at equi-effective doses were examined in the test of food intake by fed mice. Both compounds induced a significant increase of food intake, and also in these assays UFP-112 proved to be 100 fold more potent than N/OFQ. In this test, the hyperphagic effects of N/OFQ and UFP-112 are exclusively due to NOP receptor activation because such effects were present in NOP$^{+/+}$ mice but absent in NOP$^{-/-}$ mice.

Figure 2:
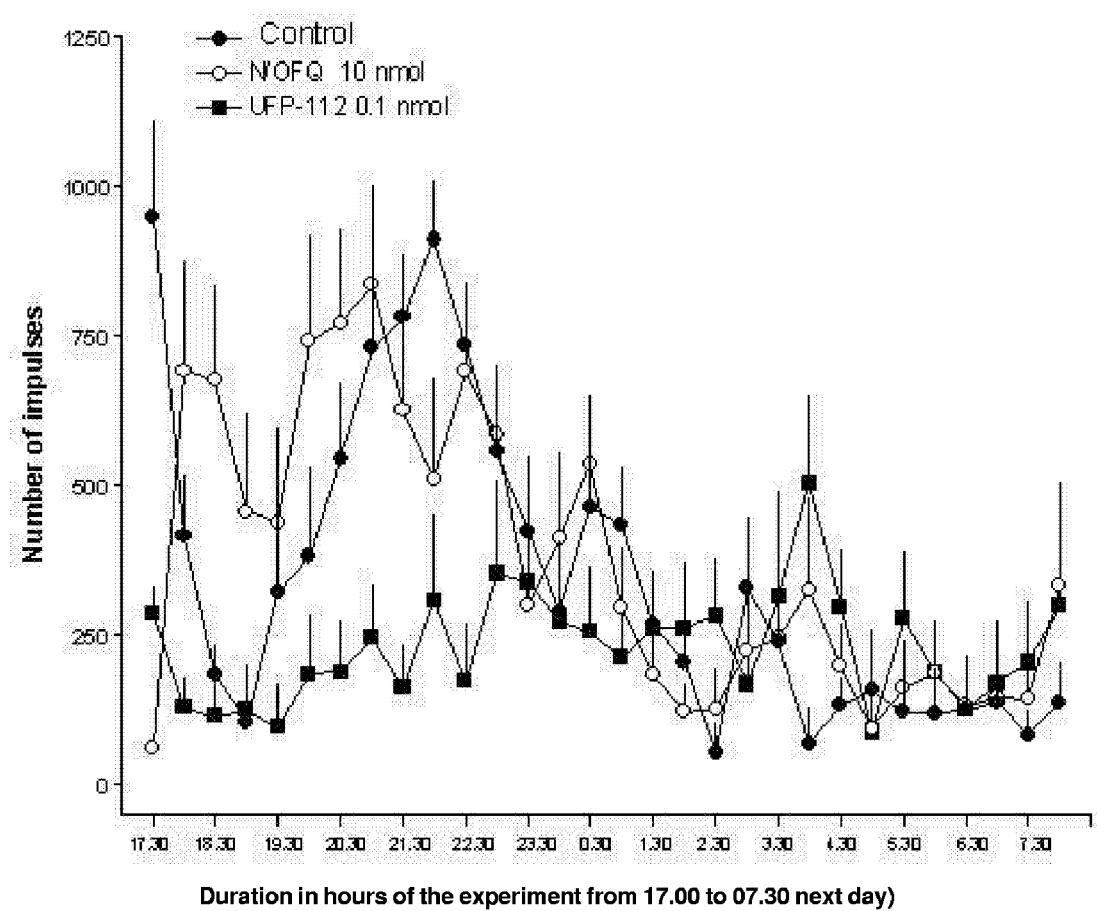
FIG. 2: Duration of the effects of N/OFQ (10 nmol/mouse) and UFP-112 (0.1 nmol/mouse), administered intracerebroventricularly (i.c.v.), on spontaneous locomotor activity in mice (ref. Rizzi et al., Naunyn Schmiedebergs Arch. Pharmacol. 363, 161-165, 2001). Control animals received one i.c.v. injection of saline (2 µl/mouse). Each point represents the mean±s.e.m. of at least 4 experiments.

In order to investigate the duration of UFP-112 action in vivo, experiments were performed in mice that compared the duration (from 5:30 p.m. to 7:30 a.m.) of the effect of equi-effective doses of N/OFQ (10 nmol) and UFP-112 (0.1 nmol), both administered i.c.v., on the spontaneous locomotor activity. Both peptides inhibited the locomotor activity, but the effect of N/OFQ ended 60 minutes after i.c.v. injection while the effect induced by UFP-112 ended after about 6 h (see FIG. 2).

4. Metabolic Stability of N/OFQ and of the New Derivatives UFP-111, UFP-112 and UFP-113 in Brain Homogenates and in the Plasma.

Plasma and brain tissue samples were obtained from male Swiss mice (Morini, Reggio Emilia, Italy, 25-30 g). The animal, sacrificed by ether anesthesia, was perfused with physiological heparin solution injected through a needle placed in the left ventricle. Blood was then withdrawn and was centrifuged at 14000×g for 2 minutes at room temperature. After separation from the pellet, the plasma was aliquoted and stocked at −80° C. After blood withdrawal, the animal was perfused further with a physiological solution for 2 minutes before brain removal. The brain tissue was homogenized in 5 vol. (w/v) of Tris/HCl (50 mM, pH 7.4, 0° C.) with a ultra-Turrax (Janke Kunkel, Staufen, FRG) 3 times for 15 seconds each. The supernatant obtained by centrifugation (3000×g for 15 min at 4° C.) was decanted and then stocked at −80° C.

The protein content of the preparations, determined by the Bradford method, as described in *Anal. Biochem.*, 72, 248-254, 1976, was approximately 8 μg/μl for the brain homogenate and 17 μg/μl for the plasma An aliquot of 100 μl solution of each peptide (3 mg/500 μl Tris) was incubated (at a final concentration of 6 μg/μl) with brain homogenate or plasma (450 μl) in a total volume of 1 ml, containing Tris/HCl 50 mM pH 7.4 buffer. Incubation of the aliquots was carried out at 37° C. for various periods up to 240 min. At different incubation times, an aliquot of the solution (100 μl) was removed and the degradation was blocked by addition of 4.5% TFA solution (200 μl). After centrifugation (3000 rpm for 15 minutes) an aliquot (100 μl) of supernatant was injected into RP-HPLC. HPLC analysis was performed in a Kromasil 100-5C18 column (4.6×250 mm) using a Beckman System Gold chromatography system equipped with a variable wave length UV detector.

The experimental conditions for elution included a gradient analysis with water (solvent A) and acetonitrile (solvent B), both containing 0.1% TFA, at a flow rate of 0.7 ml/min. The following protocol was used for gradient analysis, selected on the basis of the physico-chemical characteristics of the analyte: linear gradient from 5% to 40% B in 20 minutes; linear gradient from 40% to 60% B in 5 minutes; linear gradient from 60% to 5% B in 5 minutes. The eluate was monitored at 220 nm. The half life ($T_{1/2}$) was obtained by linear regression with the least square method, diagramming the peak areas of each derivative as a function of the incubation times, using at least five points for each analysis.

Data are shown in Table 3 as mean±standard deviation, and are obtained from at least 3 separate experiments.

TABLE 3

T½ (min) of N/OFQ and derivatives in the mouse plasma and brain tissue.

| | Plasma | Brain |
|---|---|---|
| N/OFQ | 64 ± 1 | 3.2 ± 1.8 |
| UFP-111 | 137 ± 4 | 11.0 ± 1.9 |
| UFP-112 | 167 ± 9 | 11.3 ± 1.4 |
| UFP-113 | 110 ± 10 | 12.3 ± 0.8 |

N/OFQ showed half lives in the plasma of about 1 h, which are very different compared to those obtained with the brain homogenate, which were about 3 min. All studied peptides according to the invention exhibited significantly longer half lives compared to the natural peptide. In particular, the plasma T½ of UFP-111 and UFP-113 is about twice as long as N/OFQ, while the T½ of UFP-112 is almost three-fold longer than N/OFQ.

The longer half lives exhibited by the derivatives, as compared to N/OFQ, were more pronounced in brain homogenate than in plasma. In fact, the T½ of all derivatives were more than 3-fold longer than the value exhibited by N/OFQ (3 min.) in the brain tissue.

These data show that the chemical modifications of UFP-111, 112 and 113 sequences increase their potency as agonists or antagonists, compared to N/OFQ: such modifications modulate their efficacy on the NOP receptor and determine an important reduction of susceptibility to degradation by peptidases present both in the plasma and in brain tissue. This important characteristic is certainly crucial to prolong the action of these molecules in vivo, as well-documented for UFP-112 in the series of experiments summarized in section 3 (in vivo studies).

5. Kinetics of the Inhibitory Effects of UFP-112 on Mouse Vas Deferens

Figure 3:
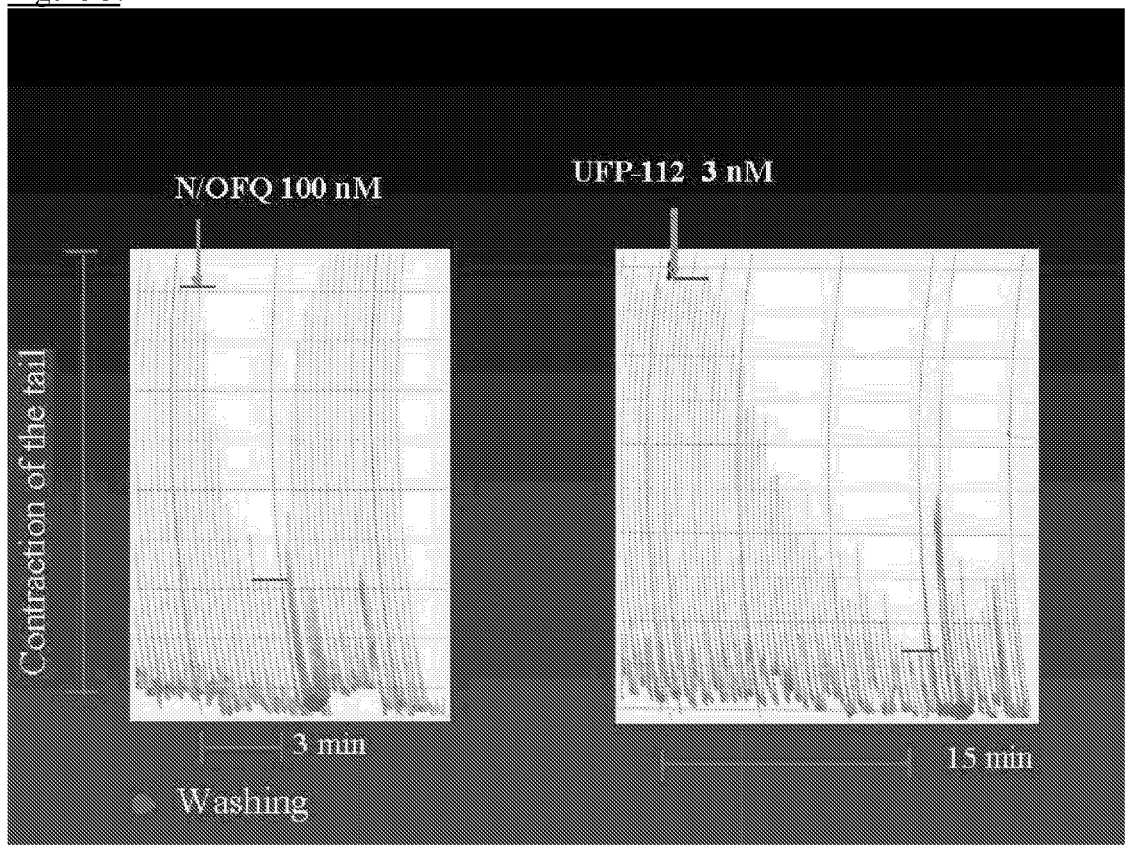
FIG. 3: Kinetics of action and reversibility of the effects of equi-effective concentrations of N/OFQ and UFP-112 in the vas deferens of mouse after electrical stimulation. Vas deferens contraction, induced by electrical stimulation, is inhibited in presence of UFP-112 or N/OFQ.

In the electrically stimulated vas deferens of mouse, both the kinetics of action of UFP-112 and the reversibility of the effects after washing were much slower than with N/OFQ (see FIG. 3). This was shown by the inhibitory effect on vas deferens contraction induced by electrical stimulation. Together with the metabolic stability data, this might explain the longer in vivo action of UFP-112 compared to the endogenous ligand N/OFQ.

6 Biological Activity of Some Compounds of Formula I in the Mouse Vas Deferens after Electrical Stimulation.

Table 4 summarizes the results obtained in the mouse vas deferens after electrical stimulation, in presence of a series of compounds of formula I, carrying different chemical modifications in position 7 and 11 of the agonist model N/OFQ-$NH_2$. These data show that different amino acidic replacements do not change the efficacy of the compounds which all act as full agonists but in some cases (for example [$Ac_5c^{11}$] N/OFQ-$NH_2$ and [D/L-Iva$^{11}$]N/OFQ-$NH_2$) increase the potency compared to the reference sequence. It should be noted that the increase in potency, obtained as result of these individual modifications (2-fold compared to the reference sequence), is lower than the increase in potency obtained as result of the combined modification at different positions, as in compound UFP-112 (table 1), whose potency increases more than 100-fold.

TABLE 4

Potency, as measured in electrically stimulated vas deferens of mouse, of a series of compounds with general formula I obtained with various chemical modifications in position 7 and 11

| Compound | pEC$_{50}$ (CL 95%) | $E_{max}$ |
|---|---|---|
| N/OFQ-NH$_2$ | 7.80 (7.74-7.86) | 93 ± 2% |
| [Ac$_3$c$^7$]N/OFQ-NH$_2$ | 7.08 (6.82-7.34) | 98 ± 1% |
| [Ac$_5$c$^7$]N/OFQ-NH$_2$ | 7.60 (7.40-7.80) | 98 ± 1% |
| [Ac$_6$c$^7$]N/OFQ-NH$_2$ | 7.20 (6.86-7.54) | 87 ± 1% |
| [(aMe)D/L-Val$^7$]N/OFQ-NH$_2$ (diastereomer 1) | 7.26 (7.00-7.52) | 88 ± 1% |
| [(aMe)D/L-Val$^7$]N/OFQ-NH$_2$ (diastereomer 2) | 7.56 (7.34-7.78) | 95 ± 1% |
| [(aMe)D/L-Leu$^7$]N/OFQ-NH$_2$ (diastereomer 1) | 7.33 (7.04-7.62) | 84 ± 1% |
| [(aMe)D/L-Leu$^7$]N/OFQ-NH$_2$ (diastereomer 2) | 7.12 (7.02-7.22) | 95 ± 2% |
| [Iva$^7$]N/OFQ-NH$_2$ (diastereomer 1) | 7.83 (7.74-7.92) | 91 ± 4% |
| [Iva$^7$]N/OFQ-NH$_2$ (diastereomer 2) | 7.62 (7.32-7.92) | 88 ± 3% |
| [Deg$^7$]N/OFQ-NH$_2$ | 7.91 (7.53-8.27) | 89 ± 2% |
| [Dpg$^7$]N/OFQ-NH$_2$ | 7.90 (7.71-8.11) | 91 ± 4% |
| [Ac$_3$c$^{11}$]N/OFQ-NH$_2$ | 7.78 (7.62-7.94) | 91 ± 4% |
| [Ac$_5$c$^{11}$]N/OFQ-NH$_2$ | 8.08 (7.93-8.23) | 89 ± 4% |
| [Ac$_6$c$^{11}$]N/OFQ-NH$_2$ | 7.79 (7.53-8.05) | 89 ± 4% |
| [(aMe)D/L-Val$^{11}$]N/OFQ-NH$_2$ (diastereomer 1) | 7.71 (7.37-8.05) | 93 ± 2% |
| [(aMe)D/L-Val$^{11}$]N/OFQ-NH$_2$ (diastereomer 2) | 7.83 (7.67-7.99) | 86 ± 4% |
| [(aMe)D/L-Leu$^{11}$]N/OFQ-NH$_2$ | 7.87 (7.67-8.07) | 91 ± 4% |
| [D/L-Iva$^{11}$]N/OFQ-NH$_2$ | 8.12 (7.78-8.46) | 90 ± 4% |
| [Deg$^{11}$]N/OFQ-NH$_2$ | 7.75 (7.43-7.89) | 87 ± 4% |
| [Dpg$^{11}$]N/OFQ-NH$_2$ | 7.53 (7.17-8.04) | 86 ± 3% |

The invention claimed is:

1. Peptide having general formula (I)

$$Xaa^1-\Psi-Gly^2-Gly^3-Xbb^4-Thr^5-Gly^6-Aib^7-Arg^8-Lys^9- \quad (I)$$
$$Ser^{10}-Ala^{11}-Arg^{12}-Lys^{13}-Arg^{14}-Lys^{15}-R$$

wherein:

when $Xaa^1$ is Phe; ψ represents the bond between the first two amino acid residues and is selected from the group consisting of CO—NH and $CH_2$—NH and $CH_2$—O; and $Xbb^4$ is pFPhe where "p" indicates the para-position in the phenyl ring of Phe; or when $Xaa^1$ is N-benzyl-glycine (Nphe), ψ represents the bond between the first two amino acid residues and is CO—NH, and $Xbb^4$ is Phe;

R represents the dipeptide Asn-Gln-$NH_2$ or an amino (—$NH_2$) terminal group;

and its pharmaceutically acceptable salts.

2. The peptide according to claim 1, wherein:

$Xaa^1$ is Phe;

ψ represents the bond between the first two amino acid residues and is selected from the group consisting of CO—NH, $CH_2$—NH or $CH_2$—O, $Xbb^4$ is pFPhe.

3. The peptide according to claim 1, wherein:

$Xaa^1$ is Phe,

ψ is CO—NH, and;

$Xbb^4$ is pFPhe.

4. A composition comprising the peptide according to claim 1.

5. A pharmaceutical composition comprising as the active principle the peptide according to claim 1 combined with pharmaceutically acceptable vehicles and/or excipients.

6. A pharmaceutical composition comprising as the active principle the peptide according to claim 1 combined with pharmaceutically acceptable vehicles and/or excipients for administration through the oral, topical, respiratory, rectal, intraspinal, intrathecal, intravesical or parenteral route.

7. A pharmaceutical composition comprising as the active principle the peptide according to claim 1 combined with pharmaceutically acceptable vehicles and/or excipients for administration through the intrathecal and/or parenteral route.

8. The peptide according to claim 1, wherein $Xaa^1$ is Phe, ψ is CO—NH, $Xbb^4$ is pFPhe and R is Asn-Gln-$NH_2$.

9. The peptide according to claim 1, wherein $Xaa^1$ is Phe, ψ is $CH_2$—NH, $Xbb^4$ is pFPhe and R is Asn-Gln-$NH_2$.

10. The peptide according to claim 1, wherein $Xaa^1$ is N-benzyl-glycine (Nphe), ψ is CO—NH, and $Xbb^4$ is Phe.

11. The peptide according to claim 1, wherein $Xaa^1$ is N-benzyl-glycine (Nphe), ψ is CO—NH, $Xbb^4$ is Phe and R is Asn-Gln-$NH_2$.

* * * * *